US008039239B2

(12) United States Patent
Reeves

(10) Patent No.: US 8,039,239 B2

(45) Date of Patent: Oct. 18, 2011

(54) RECOMBINANT MICROORGANISMS HAVING MODIFIED PRODUCTION OF ALCOHOLS AND ACIDS

(75) Inventor: Andrew Reeves, Chicago, IL (US)

(73) Assignee: Coskata, Inc., Warrenville, IL (US)

( * ) Notice: Subject to any disclaimer, the term of this patent is extended or adjusted under 35 U.S.C. 154(b) by 241 days.

(21) Appl. No.: 12/336,278

(22) Filed: Dec. 16, 2008

(65) Prior Publication Data

US 2010/0151543 A1 Jun. 17, 2010

(51) Int. Cl.

*C12P 7/06* (2006.01)
*C12P 7/16* (2006.01)
*C12N 9/04* (2006.01)
*C12N 1/20* (2006.01)
*C01B 3/00* (2006.01)

(52) U.S. Cl. ..... 435/161; 435/160; 435/190; 435/252.7; 252/373

(58) Field of Classification Search .................. 435/161, 435/160, 190, 252.7; 252/373

See application file for complete search history.

(56) References Cited

U.S. PATENT DOCUMENTS

2008/0293125 A1* 11/2008 Subbian et al. ............ 435/252.3
2009/0035848 A1* 2/2009 Hickey ....................... 435/296.1

OTHER PUBLICATIONS

Henstra et al., "Microbiology of synthesis gas fermentation for biofuel production," Curr Opin Biotechnol 18:200-206, 2007.*

Nair et al., Molecular characterization of an aldehyde/alcohol dehydrogenase gene from *Clostridium acetobutylicum*, J Bacteriol 176(3):871-885, 1994.*

Jamal Abrini, Henry Naveau, Edmond-Jacques Nyns; *Clostridium autoethanogenum*, sp. nov., an anaerobic bacterium that produces ethanol from carbon monoxide; Arch Microbiol ( 1994) 161 : 345-351; Dec. 4, 1993.

Steven P. Allen and Hans P. Blaschek; Factors involved in the electroporation-induced transformation of *Clostridium peljringens*; FEMS Microbiology Letters 70 (1990) 217-220.

M. Tyurin, R. Padda, K. X. Huang, S. Wardwell, D. Caprette, and G. N. Bennett; Electrotransformation of *Clostridium acetobutylicum* AICC 824 using high-voltage radio frequency modulated square pulses; Journal of Applied Microbiology, vol. 88, Iss. 2, pp. 220-227. 2001.

S. Barik, S. Prieto, S. B. Harrison, E. C. Clausen, J. L. Gaddy; Biological Production of Alcohols from Coal Through Indirect Liquefaction; Applied Biochemistry and Biotechnology vol. 18, No. 1, 363-378, 1988.

(Continued)

*Primary Examiner* — Rosanne Kosson

(74) *Attorney, Agent, or Firm* — McDonnell Boehnen Hulbert & Berghoff LLP

(57) ABSTRACT

Recombinant acetogenic Clostridia are engineered to modulate production of aliphatic $C_2$-$C_6$ alcohols and aliphatic $C_2$-$C_6$ organic acids from synthetic gases. One aspect of the invention provides a method of producing an aliphatic $C_2$-$C_6$ alcohol using an acetogenic *Clostridium* micro-organism having at least one genetic modification that reduces or eliminates $C_2$-$C_6$ carboxylic acid production by the modified organism. Another aspect of the invention provides a method of producing an aliphatic $C_2$-$C_6$ alcohol using an acetogenic *Clostridium* micro-organism having one or more genetic modifications that cause increased enzyme activity of carbon monoxide dehydrogenase, aldehyde ferredoxin oxidoreductase, NADPH-dependent alcohol dehydrogenase, or alcohol dehydrogenase. Yet another aspect of the invention provides a method of producing aliphatic C2-C6 alcohols using acetogenic *Clostridium* micro-organisms that have been genetically modified to increase $C_2$-$C_6$ aliphatic alcohol formation and decrease the production of the corresponding $C_2$-$C_6$ aliphatic organic acid.

4 Claims, 8 Drawing Sheets

OTHER PUBLICATIONS

Douglas Burdette and J. G. Zeikus; Purification of acetaldehyde dehydrogenase and alcohol dehydrogenases from *Thermoanaerobacter ethanolicus* 39E and characterization of the secondary-alcohol dehydrogenase (2° Adh) as a bifunctional alcohol dehydrogenase-acetyl-CoA reductive thioesterase; BioChem. J. (1994) 302, 163-170 (Printed in Great Britain).

D. Parke; Construction of mobilizable vectors derived from plasmids RP4, pUC18, and pUC19; Gene, 93 (1990), 135-137.

James G. Ferry; Co Dehydrogenase; Annual Review of Microbiology, vol. 49: 305-333 (Oct. 1995).

Edward M. Green, Zhuang L. Boynton, Latonia M. Harris, Frederick B. Rudolph, Eleftherios T. Papoutsakis, and George N. Bennett; Genetic manipulation of acid formation pathways by gene inactivation in *Clostridium acetobutylicum* ATCC 824; Microbiology (1996),142, 2079-2086.

Charles M. H. Hensgens, Wilfred R. Hagen, and Theo A. Hansen; Purification and Characterization of a Benzylviologen-Linked,Tungsten-Containing Aldehyde Oxidoreductase from *Desulfovibrio gigas*; Journal of Bacteriology, vol. 177, No. 12, Nov. 1995, 6195-6200.

Jacques Lefrancois and A. Michel Sicard; Electrotransformation of *Streptococcus pneumoniae*: evidence for restriction of DNA on entry; Microbiology (1997), 143, 523-526.

Yun-Long Lin and Hans P. Blaschek; Transformation of Heat-Treated *Clostridium acetobutylicum* Protoplasts with pUB110 Plasmid DNA; Applied and Environmental Microbiology, vol. 48. No. 4, Oct 1984, p. 737-742.

Jack S.-C. Liou, David L. Balkwill, Gwendolyn R. Drake, and Ralph S. Tanner; *Clostridium carboxidivorans* sp. nov., a solvent-producing *clostridium* isolated from an agricultural settling lagoon, and reclassification of the acetogen *Clostridium scatologenes* strain SL1 as *Clostridium drakei* sp. nov.; International Journal of Systematic and Evolutionary Microbiology (2005), 55, 2085- 2091.

Xiaoguang Liu, Ying Zhu, and Shang-Tian Yang; Construction and Characterization of ack Deleted Mutant of *Clostridium tyrobutyricum* for Enhanced Butyric Acid and Hydrogen Production; Biotechnol. Prog. 2006, 22, 1265-1275.

Dena Lyras and Julian I. Rood; Conjugative Transfer of RP4-oriT Shuttle Vectors from *Escherichia coli* to *Clostridium perfringens*; PLASMID, 39, 160-164 (1998).

Michel Monod, Claudio DeNoya, and David Dubnau; Sequence and Properties of pIM13, a Macrolide-Lincosamide-Streptogramin B Resistance Plasmid from *Bacillus subtilis*; Journal of Bacteriology, vol. 167, No. 1, Jul. 1986. p. 138-147.

Stephen W. Ragsdale; Life with Carbon Monoxide; Critical Reviews in Biochemistry and Molecular Biology, 39:165-195, 2004.

Sharon I. Reid, Errol R. Allcock, David T. Jones, and David R. Woods; Transformation of *Clostridium acetobutylicum* Protoplasts with Bacteriophage DNA; Applied & Environmental Microbiology, vol. 45. No. 1, Jan. 1983. p. 305-307.

David M. Rothstein; *Clostridium thermosaccharolyticum* Strain Deficient in Acetate Production; Journal of Bacteriology, vol. 165, No. 1, Jan. 1986, p. 319-320.

Jan Sipma, Anne M. Henstra, Sofiya N, Parshina, Piet N. L. Lens, Gatze Lettinga, Alfons J.M. Stams; Microbial CO Conversions with Applications in Synthesis Gas Purification and Bio-Desulfurization; Critical Reviews in Biotechnology, 2641-2665, (2006).

Ralph S. Tanner, Letrisa M. Miller,and Decheng Yang; *Clostridium ljungdahlii* sp. nov., an Acetogenic Species ill Clostridial rRNA Homology Group I, International Journal of Systematic Bacteriology, vol. 43. No. 2, Apr. 1993, p. 232-236.

Michael V. Tyurin, Sunil G. Desai, and Lee R. Lynd; Electrotransformation of *Clostridium thermocellum*; Applied and Environmental Microbiology, vol. 70, No. 2, Feb 2004, p. 883-890.

J. L. Vega, S. Prieto, B. B. Elmore, E. C. Clausen, and J. L. Gaddy; the Biological Production of Ethanol from Synthesis Gas; Applied Biochemistry and Biotechnology, vol. 20-21, No. 1, 781-797, 1989.

Bernard Weisblum, Madge Yang Graham, Thomas Gryczan, and David Dubnau; Plasmid Copy Number Control: Isolation and Characterization of High-Copy-Number Mutants of Plasmid pE194; Journal of Bacteriology, vol. 137, No. 1, Jan. 1979, p. 635-643.

D. Ross Williams, Danielle I. Young, and Michael Young; Conjugative plasmid transfer from *Escherichia coli* to *Clostridium acetobutylicum*; Journal of General Microbiology (1990), 136, 819-826.

DI Young, VJ Evans, JR Jefferies, KCB Jennert, ZEV Phillips, A Ravagnani and M Young; 6 Genetic Methods in *Clostridia*; Methods in Microbiology, vol. 29, 1999, pp. 191-207.

* cited by examiner

400

RECOMBINANT MICROORGANISMS HAVING MODIFIED PRODUCTION OF ALCOHOLS AND ACIDS

TECHNICAL FIELD

This invention relates generally to metabolically engineering microorganisms that use the Wood-Ljundahl pathway to produce aliphatic $C_2$-$C_6$ alcohols. More specifically, the invention relates to engineering recombinant acetogenic Clostridia to modulate production of aliphatic $C_2$-$C_6$ alcohols and aliphatic $C_2$-$C_6$ organic acids from synthesis gases.

BACKGROUND OF THE INVENTION

Synthesis gas (syngas) is a mixture of carbon monoxide (CO) gas, carbon dioxide ($CO_2$) gas, and hydrogen ($H_2$) gas, and other volatile gases such as $CH_4$, $N_2$, $NH_3$, $H_2S$ and other trace gases. Syngas is produced by gasification of various organic materials including biomass, organic waste, coal, petroleum, plastics, or other carbon containing materials. Acetogenic Clostridia microorganisms grown in an atmosphere containing syngas are capable of absorbing the syngas components CO, $CO_2$, and $H_2$ and producing aliphatic $C_2$-$C_6$ alcohols and aliphatic $C_2$-$C_6$ organic acids. These syngas components activate Wood-Ljungdahl metabolic pathway 100, shown in FIG. 1, which leads to the formation of acetyl-CoA 102, a key intermediate in the pathway. The enzymes activating Wood-Ljundahl pathway 100 are carbon monoxide dehydrogenase (CODH) 104 and hydrogenase ($H_2$ase) 106. These enzymes capture the electrons from the CO and $H_2$ in the syngas and transfer them to ferredoxin 108, an iron-sulfur (FeS) electron carrier protein. Ferredoxin 108 is the main electron carrier in Wood-Ljungdahl pathway 100 in acetogenic Clostridia, primarily because the redox potential during syngas fermentation is very low (usually between −400 and −500 mV). Upon electron transfer, ferredoxin 108 changes its electronic state from $Fe^{3+}$ to $Fe^{2+}$. Ferredoxin-bound electrons are then transferred to cofactors $NAD^+$ 110 and $NADP^+$ 112 through the activity of ferredoxin oxidoreductases 114 (FORs). The nucleotide cofactors ($NAD^+$ and $NADP^+$) are used for the generation of intermediate compounds in Wood-Ljungdahl pathway 100 leading to acetyl-CoA 102 formation.

Acetyl-CoA 102 formation through Wood-Ljungdahl pathway 100 is shown in greater detail in FIG. 2. Either $CO_2$ 202 or CO 208 provide substrates for the pathway. The carbon from $CO_2$ 202 is reduced to a methyl group through successive reductions first to formate, by formate dehydrogenase (FDH) enzyme 204, and then is further reduced to methyl tetrahydrofolate intermediate 206. The carbon from CO 208 is reduced to carbonyl group 210 by carbon monoxide dehydrogenase (CODH) 104 through a second branch of the pathway. The two carbon moieties are then condensed to acetyl-CoA 102 through the action of acetyl-CoA synthase (ACS) 212, which is part of a carbon monoxide dehydrogenase (CODH/ACS) complex. Acetyl-CoA 102 is the central metabolite in the production of $C_2$-$C_6$ alcohol s and acids in acetogenic Clostridia.

Wood-Ljungdahl pathway 100 is neutral with respect to ATP production when acetate 214 is produced (FIG. 2). When ethanol 216 is produced directly from acetyl-CoA 102, one ATP is consumed in a step involving the reduction of methylene tetrahydrafolate to methyl tetrahydrofolate 206 by a reductase, and the process is therefore net negative by one ATP. The pathway is balanced when acetyl-$PO_4$ 218 is converted to acetate 214.

Acetogenic Clostridia organisms generate cellular energy by ion gradient-driven phophorylation. When grown in a CO atmosphere, a transmembrane electrical potential is generated and used to synthesize ATP from ADP. Enzymes mediating the process include hydrogenase, NADH dehydrogenase, carbon monoxide dehydrogenase, and methylene tetrahydrofolate reductase. Membrane carriers that have been shown to be likely involved in the ATP generation steps include quinone, menaquinone, and cytochromes.

The acetogenic Clostridia produce a mixture of $C_2$-$C_6$ alcohols and acids, such as ethanol, n-butanol, hexanol, acetic acid, and butyric acid, that are of commercial interest through Wood-Ljungdahl pathway 100. For example, acetate and ethanol are produced by *C. ragsdalei* in variable proportions depending in part on fermentation conditions. However, the cost of producing the desired product, an alcohol such as ethanol, for example, could be lowered significantly if the production could be maximized by reducing or eliminating production of the corresponding acid, in this example acetate. Under some fermentation conditions, the production of acetate is best maintained within a range in which sufficient acetyl-$PO_4$ is converted to acetate to produce adequate ATP for the micro-organisms' viability without accumulation of acetic acid. It would therefore be desirable to metabolically engineer acetogenic Clostridia for improved production of selected $C_2$-$C_6$ alcohol s or acids through Wood-Ljungdahl pathway 100 by modulating enzymatic activities of key enzymes in the pathway.

SUMMARY OF THE INVENTION

One aspect of the invention provides a method of producing an aliphatic $C_2$-$C_6$ alcohol by providing an acetogenic *Clostridium* micro-organism having a genetic modification within at least one transcriptional unit that substantially reduces $C_2$-$C_6$ carboxylic acid production by the organism. A growth medium and a syngas are supplied, and the modified acetogenic *Clostridium* micro-organism is cultured in the growth medium in the presence of the syngas to produce the aliphatic $C_2$-$C_6$ alcohol.

Another aspect of the invention provides a method of producing an aliphatic $C_2$-$C_6$ alcohol by providing an acetogenic *Clostridium* micro-organism having a genetic modification within at least one transcriptional unit that increases aliphatic $C_2$-$C_6$ alcohol production by the micro-organism. A growth medium and a syngas are supplied, and the modified acetogenic *Clostridium* micro-organism is cultured in the growth medium in the presence of the syngas to produce the aliphatic $C_2$-$C_6$ alcohol.

Another aspect of the invention provides a method of producing an aliphatic $C_2$-$C_6$ alcohol by providing a *Clostridium* micro-organism having at least two transcriptional units. A genetic modification within the first transcriptional unit substantially reduces aliphatic $C_2$-$C_6$ carboxylic acid production, and a second genetic modification within the second transcriptional unit substantially increases aliphatic $C_2$-$C_6$ alcohol production by the micro-organism. A growth medium and a syngas are supplied, and the modified acetogenic *Clostridium* micro-organism is cultured in the growth medium in the presence of the syngas to produce the aliphatic $C_2$-$C_6$ alcohol.

Yet another aspect of the invention provides a method of producing butanol by providing *Clostridium carboxidivorans* having at least one genetic modification that reduces or eliminates butyrate production by the organism. A growth medium and a syngas are supplied, and the modified *Clostridium*

*carboxidivroans* organism is cultured in the growth medium in the presence of the syngas to produce butanol.

The present invention is illustrated by the accompanying figures portraying various embodiments and the detailed description given below. The figures should not be taken to limit the invention to the specific embodiments, but are for explanation and understanding. The detailed description and figures are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying figures.

DETAILED DESCRIPTION

The present invention is directed to acetogenic Clostridia micro-organisms that have been genetically modified to increase production of aliphatic $C_2$-$C_6$ alcohols. Alcohol production can be increased by either increasing expression of a transcriptional unit that increases alcohol production or decreasing expression of a transcriptional unit needed for production of a $C_2$-$C_6$ carboxylic acid. A transcriptional unit is either a gene, a single unit, that codes for one enzyme and is controlled by a promoter, or an operon, a multiple transcriptional unit, that codes for two or more genes, and whose total gene expression is controlled by the same promoter. For example alcohol production can be increased by either increasing transcription of the gene that codes for NADPH-dependent alcohol dehydrogenase, or by reducing or eliminating transcription of the operon that codes for acetate kinase and phosphotransacetylase, and by this means, reducing production of the corresponding $C_2$-$C_6$ organic acid.

Several species of acetogenic Clostridia that produce $C_2$-$C_6$ alcohols and acids via the Wood-Ljungdahl pathway have been characterized: *C. ragsdahlei, C. ljungdahlii, C. carboxydivorans,* and *C. autoethanogenum.* The genomes of three of these micro-organisms were sequenced in order to locate and modify the portions of the genome that code for the enzymes of interest.

Figure 1:
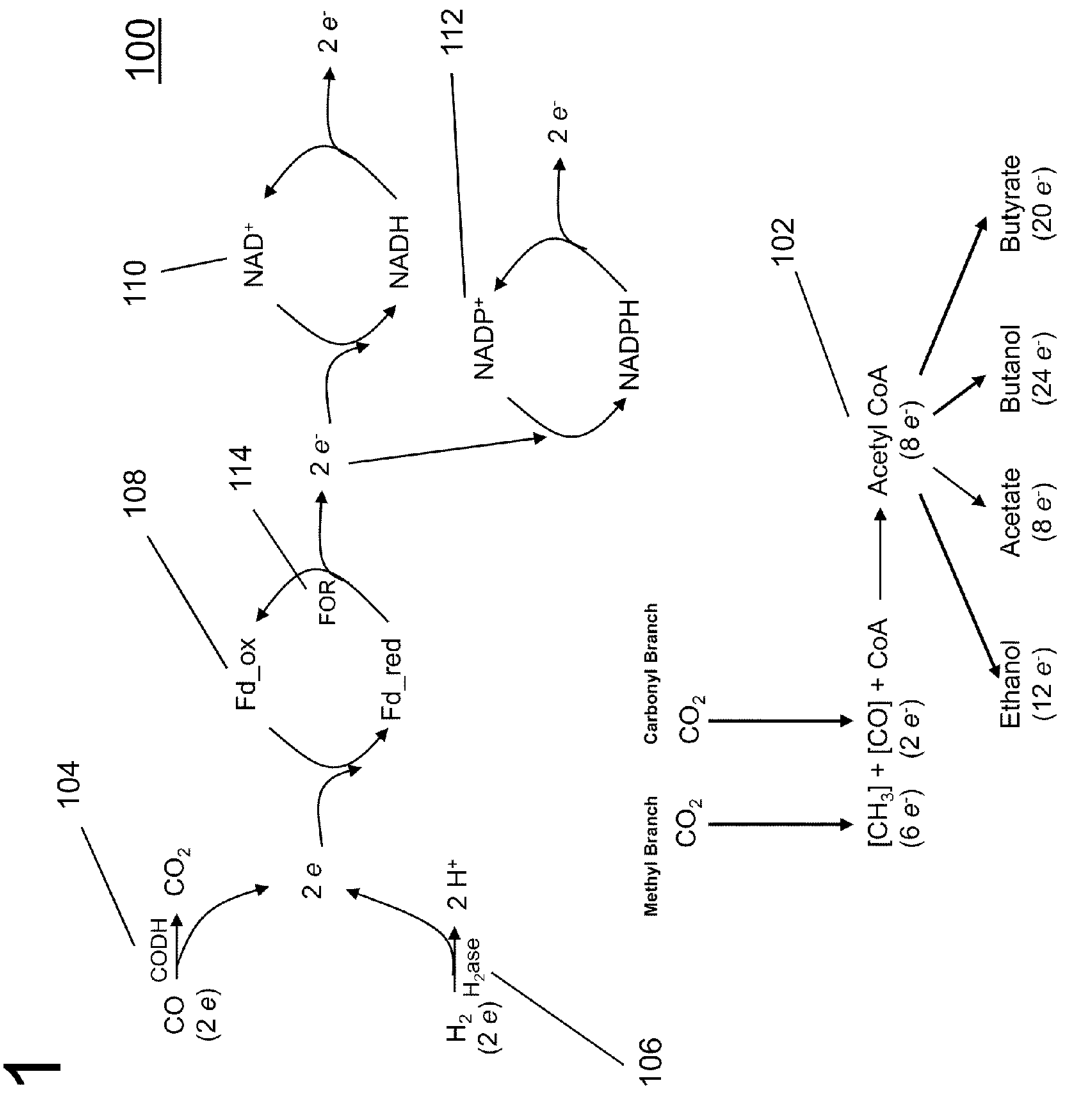
FIG. 1 is a diagram illustrating the electron flow pathway during syngas fermentation in acetogenic Clostridia including some of the key enzymes involved in the process.
Figure 2:
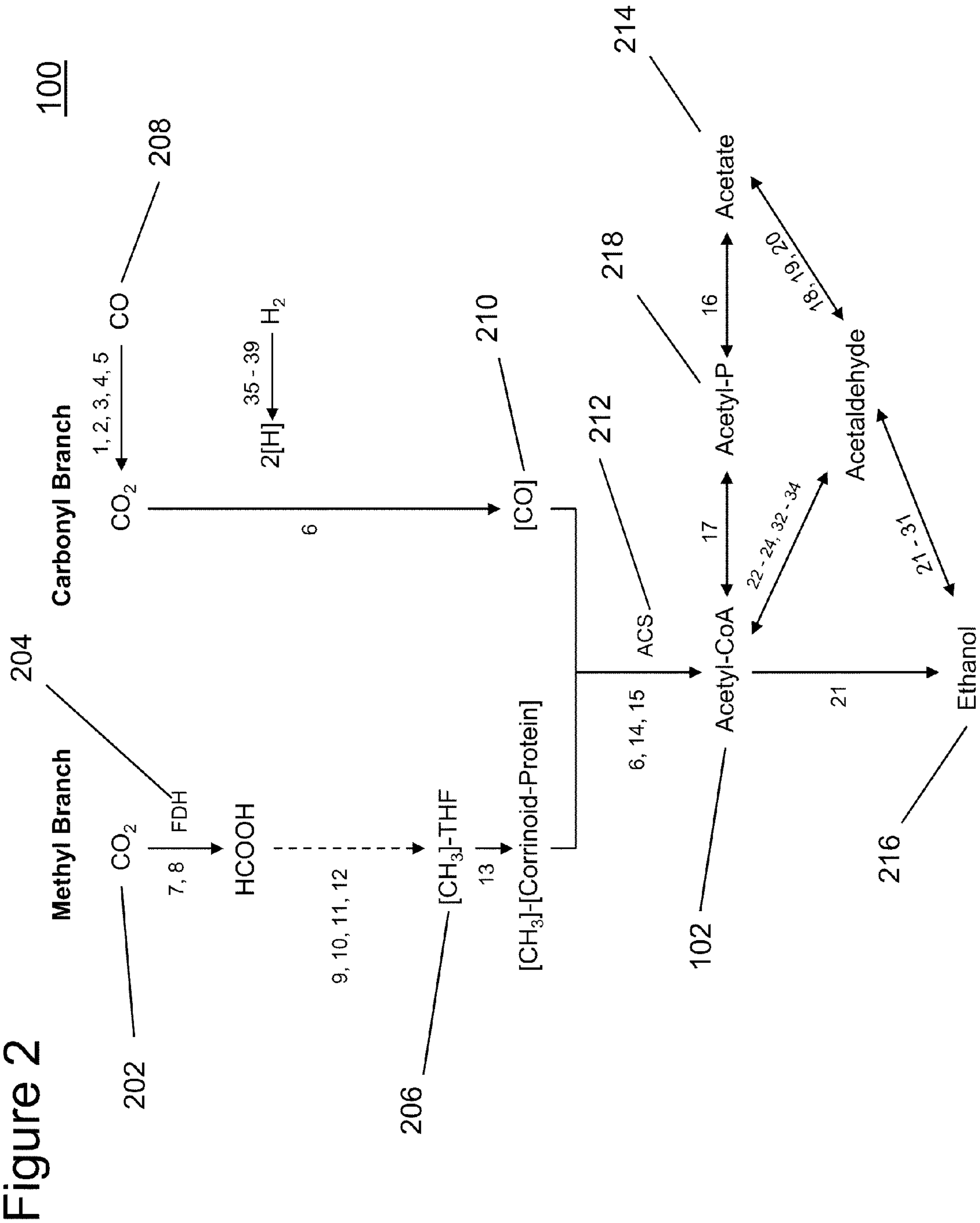
FIG. 2 is a diagram illustrating the Wood-Ljungdahl ($C_1$) pathway for acetyl-CoA production and the enzymatic conversion of acetyl-CoA to acetate and ethanol.

The genes that code for enzymes in the Wood-Ljungdahl metabolic pathway and ethanol synthesis identified in the *C. ragsdahlei* genome are presented in Table 1. The first column identifies the pathway associated with each gene. The gene identification numbers indicated in the second column correspond to the numbers representing the enzymes involved in the metabolic reactions in the Wood-Ljungdahl pathway shown in FIG. 1 and FIG. 2.

TABLE 1

*Clostridium ragsdalei* genes used in metabolic engineering.

| Pathway | Gene ID | Gene Name | EC number | ORF ID | Copy ID | Description |
|---|---|---|---|---|---|---|
| Wood-Ljungdahl | 1 | Carbon Monoxide Dehydrogenase | 1.2.2.4 | RCCC00183 | CODH_1 | CO oxidation |
| | 2 | | | RCCC01175 | CODH_2 | CO oxidation |
| | 3 | | | RCCC01176 | CODH_3 | CO oxidation |
| | 4 | | | RCCC02026 | CODH_4 | CO oxidation |
| | 5 | | | RCCC03874 | CODH_5 | CO oxidation |
| | 6 | Carbon Monoxide Dehydrogenase/Acetyl-CoA Synthase | 1.2.99.2 | RCCC03862 | cooS/acsA | bifunctional CODH/ACS enzyme, carbon fixation |
| | 7 | Formate Dehydrogenase | 1.2.1.2 | RCCC00874 | FDH_1 | Methyl branch carbon fixation |
| | 8 | | | RCCC03324 | FDH_2 | |
| | 9 | Formyltetrahydrofolate Synthase | 6.3.4.3 | RCCC03872 | FTHFS | Methyl branch carbon fixation |
| | 10 | Methenyltetrahydrofolate cyclohydrolase | 3.5.4.9 | RCCC03870 | MEC | Methyl branch carbon fixation |

TABLE 1-continued

*Clostridium ragsdalei* genes used in metabolic engineering.

| Pathway | Gene ID | Gene Name | EC number | ORF ID | Copy ID | Description |
|---|---|---|---|---|---|---|
| | 11 | Methylenetetrahydrofolate dehydrogenase | 1.5.1.5 | RCCC03870 | MED | Methyl branch carbon fixation |
| | 12 | Methylenetetrahydrofolate reductase | 1.5.1.20 | RCCC03868 | MER | Methyl branch carbon fixation |
| | 13 | Methyltransferase | 2.1.1.13 | RCCC03863 | acsE | Methyl branch carbon fixation |
| | 14 | Corrinoid/Iron-sulfur protein | 1.2.99.2 | RCCC03864 | acsC | Part of CODH/ACS complex, Large subunit |
| | 15 | Corrinoid/Iron-sulfur protein | 1.2.99.2 | RCCC03865 | acsD | Part of CODH/ACS complex, Small subunit |
| Ethanol and acetate production | 16 | Acetate Kinase | 2.7.2.1 | RCCC01717 | ACK | Acetate production |
| | 17 | Phospho-transacetylase | 2.3.1.8 | RCCC01718 | PTA | Acetate production |
| | 18 | Tungsten-containing aldehyde ferredoxin oxidoreductase | 1.2.7.5 | RCCC00020 | AOR_1 | Reduction of acetate to acetaldehyde |
| | 19 | | 1.2.7.5 | RCCC00030 | AOR_2 | Reduction of acetate to acetaldehyde |
| | 20 | | 1.2.7.5 | RCCC01183 | AOR_3 | Reduction of acetate to acetaldehyde |
| | 21 | Alcohol Dehydrogenase | 1.1.1.2 | RCCC02715 | ADH_1 | zinc containing, NADPH dependent secondary ADH |
| | 22 | | 1.1.1.1 | RCCC01356 | ADH_2 | two pfam domain: FeADH and ALDH, AdhE |
| | 23 | | 1.1.1.1 | RCCC01357 | ADH_3 | two pfam domain: FeADH and ALDH, AdhE |
| | 24 | | 1.1.1.1 | RCCC01358 | ADH_4 | two pfam domain: FeADH and ALDH, AdhE, fragment (76aa) |
| | 25 | | 1.1.1.1 | RCCC03300 | ADH_5 | one pfam domain: FeADH |
| | 26 | | 1.1.1.1 | RCCC03712 | ADH_6 | one pfam domain: FeADH |
| | 27 | | 1.1.1.1 | RCCC04095 | ADH_7 | one pfam domain: FeADH |
| | 28 | | 1.—.—.— | RCCC00004 | ADH_8 | short chain ADH, multiple copy |
| | 29 | | 1.—.—.— | RCCC01567 | ADH_9 | short chain ADH, multiple copy |
| | 30 | | 1.—.—.— | RCCC02765 | ADH_10 | short chain ADH, multiple copy |
| | 31 | | 1.—.—.— | RCCC02240 | ADH_11 | short chain ADH, multiple copy |
| | 32 | Aldehyde | 1.2.1.10 | RCCC03290 | ALDH_1 | Acetylating |
| | 33 | Dehydrogenase | 1.2.1.10 | RCCC04101 | ALDH_2 | Acetylating |
| | 34 | | 1.2.1.10 | RCCC04114 | ALDH_3 | Acetylating |
| Hydrogenase | 35 | Hydrogenase | 1.12.7.2 | RCCC00038 | HYD_1 | Fe only, H2 production |
| | 36 | | 1.12.7.2 | RCCC00882 | HYD_2 | Fe only, large subunit, H2 production |
| | 37 | | 1.12.7.2 | RCCC01252 | HYD_3 | Fe only, H2 production |
| | 38 | | 1.12.7.2 | RCCC01504 | HYD_4 | Fe only, H2 production |
| | 39 | | 1.12.7.2 | RCCC02997 | HYD_5 | Ni—Fe large subunit, H2 oxidation |
| Electron carrier | 40 | Ferredoxin | | RCCC00086 | | |
| | 41 | | | RCCC00301 | | |
| | 42 | | | RCCC00336 | | |
| | 43 | | | RCCC01168 | | |
| | 44 | | | RCCC01415 | | |
| | 45 | | | RCCC01825 | | |

TABLE 1-continued

| *Clostridium ragsdalei* genes used in metabolic engineering. | | | | | | |
|---|---|---|---|---|---|---|
| Pathway | Gene ID | Gene Name | EC number | ORF ID | Copy ID | Description |
| | 46 | | | RCCC02435 | | |
| | 47 | | | RCCC02890 | | |
| | 48 | | | RCCC03063 | | |
| | 49 | | | RCCC03726 | | |
| | 50 | | | RCCC04003 | | |
| | 51 | | | RCCC04147 | | |
| Electron transfer | 52 | Pyridine nucleotide-disulphide oxidoreductases | | RCCC02615 | | glutamate synthase small chain, but no large chain next to it |
| | 53 | | | RCCC02028 | | next to cooF and cooS, probably important for reduced pyridine cofactor generation |
| | 54 | | | RCCC03071 | | NADH dehydrogenase, not part of an operon |
| | 55 | Membrane-associated electron transfer FeS protein, cooF | | RCCC02027 | cooF | Between gene number 4 and gene number 53 |

Sequence analysis of the *C. ljungdahlii* genome was conducted. Genes coding for enzymes in the Wood-Ljungdahl pathway, ethanol and acetate production, and electron transfer have been identified and located within the genome. The results are presented in Table 2.

TABLE 2

| *Clostridium ljungdahlii* genes used in metabolic engineering. | | | | | | |
|---|---|---|---|---|---|---|
| Pathway | Gene ID | Gene Name | EC number | ORE ID | Copy ID | Description |
| Wood-Ljungdahl | 1 | Carbon Monoxide Dehydrogenase | 1.2.2.4 | RCCD00983 | CODH_1 | CO oxidation |
| | 2 | | | RCCD00984 | CODH_2 | CO oxidation |
| | 3 | | | RCCD01489 | CODH_3 | CO oxidation |
| | 4 | | | RCCD04299 | CODH_4 | CO oxidation |
| | 5 | Carbon Monoxide Dehydrogenase/Acetyl-CoA Synthase | 1.2.99.2 | RCCD00972 | CODH_ACS | bifunctional CODH/ACS enzyme, carbon fixation |
| | 6 | Formate Dehydrogenase | 1.2.1.2 | RCCD01275 | FDH_1 | Methyl branch |
| | 7 | | | RCCD01472 | FDH_2 | carbon fixation |
| | 8 | Formyltetrahydrofolate Synthase | 6.3.4.3 | RCCD00982 | FTHFS | Methyl branch carbon fixation |
| | 9 | Methenyltetrahydrofolate cyclohydrolase | 3.5.4.9 | RCCD00980 | MEC | Methyl branch carbon fixation |
| | 10 | Methylenetetrahydrofolate dehydrogenase | 1.5.1.5 | RCCD00980 | MED | Methyl branch carbon fixation |
| | 11 | Methylenetetrahydrofolate reductase | 1.5.1.20 | RCCD00978 | MER | Methyl branch carbon fixation |
| | 12 | Methyltransferase | 2.1.1.13 | RCCD00973 | MET | Methyl branch carbon fixation |
| | 13 | Corrinoid/Iron-sulfur protein | 1.2.99.2 | RCCD00974 | COPL | Part of CODH/ACS complex, Large subunit |
| | 14 | Corrinoid/Iron-sulfur protein | 1.2.99.2 | RCCD00975 | COPS | Part of CODH/ACS complex, Small subunit |
| Ethanol and acetate production | 15 | Acetate Kinase | 2.7.2.1 | RCCD02720 | ACK | Acetate production |
| | 16 | Phospho-transacetylase | 2.3.1.8 | RCCD02719 | PTA | Acetate production |
| | 17 | Tungsten-containing aldehyde ferredoxin oxidoreductase | 1.2.7.5 | RCCD01679 | AOR_1 | Reduction of acetate to acetaldehyde |
| | 18 | | 1.2.7.5 | RCCD01692 | AOR_2 | Reduction of acetate to acetaldehyde |

TABLE 2-continued

*Clostridium ljungdahlii* genes used in metabolic engineering.

| Pathway | Gene ID | Gene Name | EC number | ORE ID | Copy ID | Description |
|---|---|---|---|---|---|---|
| | 19 | Alcohol Dehydrogenase | 1.1.1.2 | RCCD00257 | ADH_1 | zinc containing, NADPH dependent secondary ADH |
| | 20 | | 1.1.1.1 | RCCD00167 | ADH_2 | two pfam domain: FeADH and ALDH, AdhE |
| | 21 | | 1.1.1.1 | RCCD00168 | ADH_3 | two pfam domain: FeADH and ALDH, AdhE |
| | 22 | | 1.1.1.1 | RCCD02628 | ADH_5 | one pfam domain: FeADH |
| | 23 | | 1.1.1.1 | RCCD03350 | ADH_7 | one pfam domain: FeADH |
| | 24 | | 1.—.—.— | RCCD00470 | ADH_8 | short chain ADH, multiple copy |
| | 25 | | 1.—.—.— | RCCD01665 | ADH_9 | short chain ADH, multiple copy |
| | 26 | | 1.—.—.— | RCCD01767 | ADH_10 | short chain ADH, multiple copy |
| | 27 | | 1.—.—.— | RCCD02864 | ADH_11 | short chain ADH, multiple copy |
| | 28 | Aldehyde Dehydrogenase | 1.2.1.10 | RCCD02636 | ALDH_1 | Acetylating |
| | 29 | | 1.2.1.10 | RCCD03356 | ALDH_2 | Acetylating |
| | 30 | | 1.2.1.10 | RCCD03368 | ALDH_3 | Acetylating |
| Hydrogenase | 31 | Hydrogenase | 1.12.7.2 | RCCD00346 | HYD_1 | Ni—Fe large subunit, H2 oxidation |
| | 32 | | 1.12.7.2 | RCCD00938 | HYD_2 | Ni—Fe small subunit, H2 oxidation |
| | 33 | | 1.12.7.2 | RCCD01283 | HYD_3 | Fe only, large subunit, H2 production |
| | 34 | | 1.12.7.2 | RCCD01700 | HYD_4 | Fe only, H2 production |
| | 35 | | 1.12.7.2 | RCCD02918 | HYD_5 | Fe only, H2 production |
| | 36 | | 1.12.7.2 | RCCD04233 | HYD_6 | Fe only, H2 production |
| Electron carrier | 37 | Ferredoxin | | RCCD00424 | | |
| | 38 | | | RCCD01226 | | |
| | 39 | | | RCCD01932 | | |
| | 40 | | | RCCD02185 | | |
| | 41 | | | RCCD02239 | | |
| | 42 | | | RCCD02268 | | |
| | 43 | | | RCCD02580 | | |
| | 44 | | | RCCD03406 | | |
| | 45 | | | RCCD03640 | | |
| | 46 | | | RCCD03676 | | |
| | 47 | | | RCCD04306 | | |
| Electron transfer | 48 | Pyridine nucleotide-disulphide oxidoreductases | | RCCD00185 | | glutamate synthase small chain, but no large chain next to it |
| | 49 | | | RCCD01487 | | next to cooF and cooS, probably important for reduced pyridine cofactor generation |

TABLE 2-continued

*Clostridium ljungdahlii* genes used in metabolic engineering.

| Pathway | Gene ID | Gene Name | EC number | ORE ID | Copy ID | Description |
|---|---|---|---|---|---|---|
| | 50 | | | RCCD00433 | | NADH dehydrogenase, not part of an operon |
| | 51 | Membrane-associated electron transfer FeS protein, cooF | | RCCD01488 | cooF | Between gene number 3 and gene number 49 |

Similarly, the genome of *C. carboxydivorans* was sequenced, and genes coding for the enzymes in the Wood-Ljungdahl pathway and ethanol and acetate synthesis were identified and located. The results are presented in Table 3.

TABLE 3

*Clostridium carboxidivorans* genes used in metabolic engineering.

| Pathway | Gene ID | Gene Name | EC number | ORF ID | Copy ID | Description |
|---|---|---|---|---|---|---|
| Wood-Ljungdahl | 1 | Carbon Monoxide Dehydrogenase | 1.2.2.4 | RCCB04039 | CODH_1 | CO oxidation |
| | 2 | | | RCCB01154 | CODH_2 | CO oxidation |
| | 3 | | | RCCB02478 | CODH_3 | CO oxidation |
| | 4 | | | RCCB03963 | CODH_4 | CO oxidation |
| | 5 | | | RCCB04038 | CODH_5 | CO oxidation |
| | 6 | Carbon Monoxide Dehydrogenase/Acetyl-CoA Synthase | 1.2.99.2 | RCCB04293 | CODH_ACS | bifunctional CODH/ACS enzyme, carbon fixation |
| | 7 | Formate Dehydrogenase | 1.2.1.2 | RCCB05406 | FDH_1 | Methyl branch |
| | 8 | | | RCCB01346 | FDH_2 | carbon fixation |
| | 9 | Formyltetrahydrofolate Synthase | 6.3.4.3 | RCCB04040 | FTHFS | Methyl branch carbon fixation |
| | 10 | Methenyltetrahydrofolate cyclohydrolase | 3.5.4.9 | RCCB04042 | MEC | Methyl branch carbon fixation |
| | 11 | Methylenetetrahydrofolate dehydrogenase | 1.5.1.5 | RCCB04042 | MED | Methyl branch carbon fixation |
| | 12 | Methylenetetrahydrofolate reductase | 1.5.1.20 | RCCB04044 | MER | Methyl branch carbon fixation |
| | 13 | Methyltransferase | 2.1.1.13 | RCCB04294 | MET | Methyl branch carbon fixation |
| | 14 | Corrinoid/Iron-sulfur protein | 1.2.99.2 | RCCB04049 | COPL | Part of CODH/ACS complex, Large subunit |
| | 15 | Corrinoid/Iron-sulfur protein | 1.2.99.2 | RCCB04047 | COPS | Part of CODH/ACS complex, Small subunit |
| Ethanol and acetate production | 16 | Acetate Kinase | 2.7.2.1 | RCCB05249 | ACK | Acetate production |
| | 17 | Phospho-transacetylase | 2.3.1.8 | RCCB02481 | PTA | Acetate production |
| | 18 | Tungsten-containing aldehyde ferredoxin oxidoreductase | 1.2.7.5 | RCCB00063 | AOR_1 | Reduction of acetate to acetaldehyde |
| | 19 | Alcohol Dehydrogenase | 1.1.1.2 | RCCB03584 | ADH_1 | zinc-ADH |
| | 20 | | 1.1.1.1 | RCCB03870 | ADH_2 | two pfam domain: FeADH and ALDH, AdhE |
| | 21 | | 1.1.1.1 | RCCB05675 | ADH_3 | truncated, AdhE |
| | 22 | | 1.1.1.1 | RCCB00958 | ADH_5 | one pfam domain: FeADH |
| | 23 | | 1.1.1.1 | RCCB04489 | ADH_6 | one pfam domain: FeADH |
| | 24 | | 1.1.1.1 | RCCB04503 | ADH_7 | one pfam domain: FeADH |
| | 25 | | 1.—.—.— | RCCB02465 | ADH_9 | short chain ADH, multiple copy |
| | 26 | | 1.—.—.— | RCCB05551 | ADH_10 | short chain ADH, multiple copy |
| | 27 | Aldehyde Dehydrogenase | 1.2.1.10 | RCCB02403 | ALDH_1 | Acetylating |
| | 28 | | 1.2.1.10 | RCCB02561 | ALDH_2 | Acetylating |
| | 29 | | 1.2.1.10 | RCCB04031 | ALDH_3 | Acetylating |
| Hydrogenase | 30 | Hydrogenase | 1.12.7.2 | RCCB02249 | HYD_1 | Ni—Fe large subunit, H2 oxidation |
| | 31 | | 1.12.7.2 | RCCB01319 | HYD_2 | Fe only, H2 production |

TABLE 3-continued

| *Clostridium carboxidivorans* genes used in metabolic engineering. | | | | | | |
|---|---|---|---|---|---|---|
| Pathway | Gene ID | Gene Name | EC number | ORF ID | Copy ID | Description |
| | 32 | | 1.12.7.2 | RCCB01405 | HYD__3 | Fe only, H2 production |
| | 33 | | 1.12.7.2 | RCCB01516 | HYD__4 | Fe only, large subunit, H2 production |
| | 34 | | 1.12.7.2 | RCCB03483 | HYD__5 | Fe only, H2 production |
| | 35 | | 1.12.7.2 | RCCB05411 | HYD__6 | Fe only, large subunit, H2 production |
| Electron carrier | 36 | Ferredoxin | | RCCB00234 | | |
| | 37 | | | RCCB00345 | | |
| | 38 | | | RCCB01260 | | |
| | 39 | | | RCCB01334 | | |
| | 40 | | | RCCB01775 | | |
| | 41 | | | RCCB01960 | | |
| | 42 | | | RCCB01972 | | |
| | 43 | | | RCCB02618 | | |
| | 44 | | | RCCB02638 | | |
| | 45 | | | RCCB02836 | | |
| | 46 | | | RCCB02853 | | |
| | 47 | | | RCCB03023 | | |
| | 48 | | | RCCB03191 | | |
| | 49 | | | RCCB03278 | | |
| | 50 | | | RCCB03452 | | |
| | 51 | | | RCCB03596 | | |
| | 52 | | | RCCB03762 | | |
| | 53 | | | RCCB03972 | | |
| | 54 | | | RCCB04165 | | |
| | 55 | | | RCCB04383 | | |
| | 56 | | | RCCB04571 | | |
| | 57 | | | RCCB04585 | | |
| | 58 | | | RCCB05780 | | |
| | 59 | | | RCCB05975 | | |
| | 60 | | | RCCB06304 | | |
| | 61 | | | RCCB06305 | | |
| Electron transfer | 62 | Pyridine nucleotide-disulphide oxidoreductases | | RCCB00442 | | NADH dehydrogenase, not part of an operon |
| | 63 | | | RCCB01674 | | NADH dehydrogenase, not part of an operon |
| | 64 | | | RCCB03510 | | next to cooF and cooS, probably important for reduced pyridine cofactor generation |
| | 65 | | | RCCB00586 | | NADH dehydrogenase, not part of an operon |
| | 66 | | | RCCB04795 | | NADH:ferredoxin oxidoreductase, not part of an operon |
| | 67 | Membrane-associated electron transfer FeS protein, cooF | | RCCB03509 | cooF | Between gene number 2 and gene number 64 |

In addition to ethanol synthesis, *C. carboxydivorans* produces butanol, butyrate, hexanol and hexanoate. The genes coding for the enzymes in the butanol/butyrate synthetic pathway were identified and located within the genome of *C. carboxydivorans* as shown in Table 4.

TABLE 4

*Clostridium carboxidivorans* butanol production genes

| Pathway | Gene ID | Gene Name | EC number | ORF ID | Copy ID | Description |
|---|---|---|---|---|---|---|
| Butanol production | 70 | Acetyl-CoA acetyltransferase | 2.3.1.9 | RCCB05104 | | |
| | 71 | | | RCCB06240 | | |
| | 72 | | | RCCB04397 | | |
| | 73 | 3-hydroxybutyryl-CoA dehydrogenase | 1.1.1.157 | RCCB05103 | | |
| | 74 | | | RCCB03354 | | |
| | 75 | 3-hydroxyacyl-CoA dehydrogenase | 1.1.1.35 | RCCB01361 | | |
| | 76 | 3-hydroxybutyryl-CoA dehydratase | 4.2.1.55 | RCCB03353 | | |
| | 77 | | | RCCB05102 | | |
| | 78 | Butyryl-CoA dehydrogenase | 1.3.99.2 | RCCB01169 | | |
| | 79 | | | RCCB05105 | | |
| | 80 | | | RCCB03214 | | |
| | 81 | | | RCCB01307 | | |
| | 82 | | | RCCB00309 | | |
| | 83 | | | RCCB04399 | | |
| | 84 | Phosphate butyryltransferase | 2.3.1.19 | RCCB03974 | | |
| | 85 | | | RCCB01389 | | |
| | 86 | Butyrate kinase | 2.7.2.7 | RCCB01073 | | |
| | 87 | | | RCCB00672 | | |
| | 88 | | | RCCB03973 | | |
| | 89 | Butanal/butanol dehydrogenase | 1.2.1.57 | RCCB05526 | | |
| | 90 | | | RCCB05675 | | |
| | 91 | | | RCCB03870 | | |

Genes that code for enzymes in the electron transfer pathway include carbon monoxide dehydrogenase, Enzyme Commission number (EC 1.2.2.4). Five separate open reading frame (ORF) sequences were identified in *C. ragsdalei* and *C. ljungdahlii,* and six were identified in the *C. carboxidivorans* genome for the carbon monoxide dehydrogenase enzyme.

Figure 3:
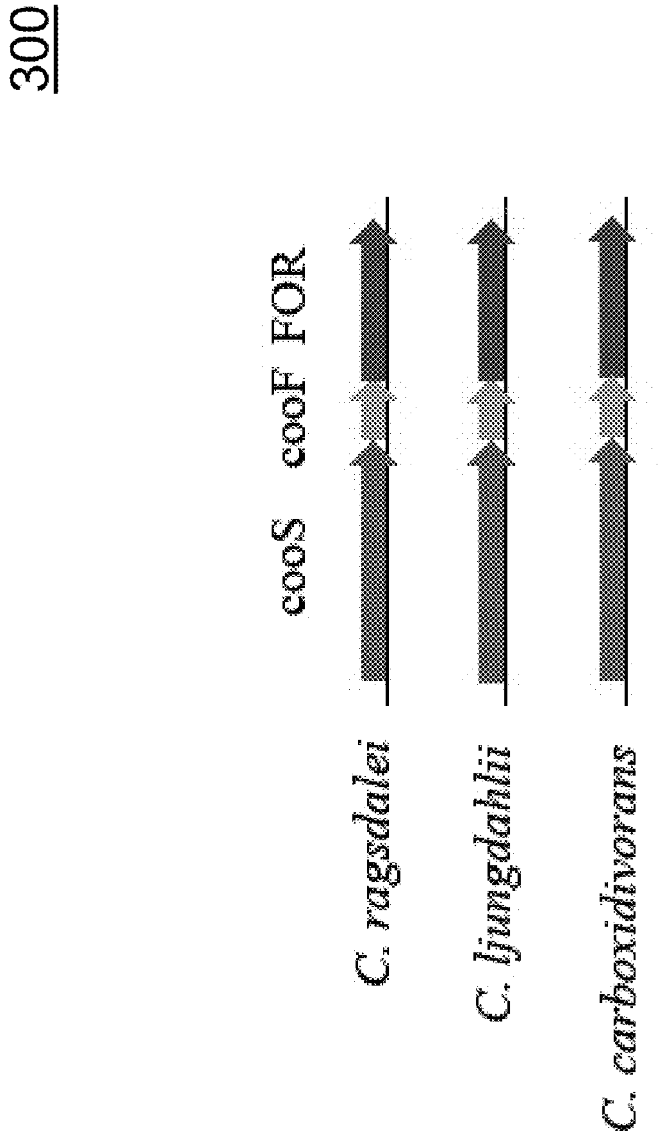
FIG. 3 is a diagram illustrating a genetic map containing the location of one of the carbon monoxide dehydrogenase (CODH) operons which includes cooS, cooF and a ferredoxin oxidoreductase (FOR), in accordance with the invention.

FIG. 3 is a diagram of carbon-monoxide dehydrogenase operon 300. The gene order within operon 300 is highly conserved in all three species of acetogenic Clostridia, and comprises the genes coding for the carbon monoxide dehydrogenase (cooS) (Gene ID 4, Tables 1, 2, and 3), followed by the membrane-associated electron transfer FeS protein (cooF) (Gene ID 55, Table 1; Gene ID 51, Table 2; Gene ID 67, Table 3), in turn, followed by ferredoxin oxidoreductase (FOR).

Six hydrogenase (EC 1.12.7.2) ORF sequences were identified in the genome of each of the acetogenic *Clostridium* species.

Twelve ferredoxin biosynthesis genes (Gene ID 40-51, Table 1) were identified in the *C. ragsdalei* genome. Eleven ferredoxin biosynthesis genes (Gene ID 37-47, Table 2) were found in *C. ljungdahlii,* and twenty-six (Gene ID 36-61, Table 3) were found in *C. carboxidivorans.*

Three genes coding for ferredoxin oxidoreductase enzymes were found in the *C. ragsdalei* genome that contain both a ferredoxin and nicotinamide cofactor binding domain. The ORF Sequence ID numbers (Table 1) for these genes are: RCCC02615; RCCC02028; and RCCC03071. The potentially key gene for metabolic engineering, RCCC02028, is part of the cooS/cooF operon, also shown in FIG. 3. Similarly, three genes coding for ferredoxin oxidoreductase (FOR) enzymes were found in the *C. ljungdahlii* genome. Each of these genes code for both the ferredoxin and cofactor binding domains. The ORF Sequence ID numbers for these genes are: RCCD00185; RCCD01847; and RCCD00433 (Table 2). The potentially key gene RCCD01847, is part of the cooF/cooS operon shown in FIG. 3.

Five genes were found in the *C. carboxidivorans* genome that contain both the ferredoxin and cofactor binding domains. The ORF Sequence ID numbers (Table 3) for these genes are: RCCB00442; RCCB01674; RCCB03510; RCCB00586; and RCCB 04795. The potentially key gene for modulating electron flow is RCCB03510, which is part of the cooF/cooS operon (FIG. 3).

Figure 4:
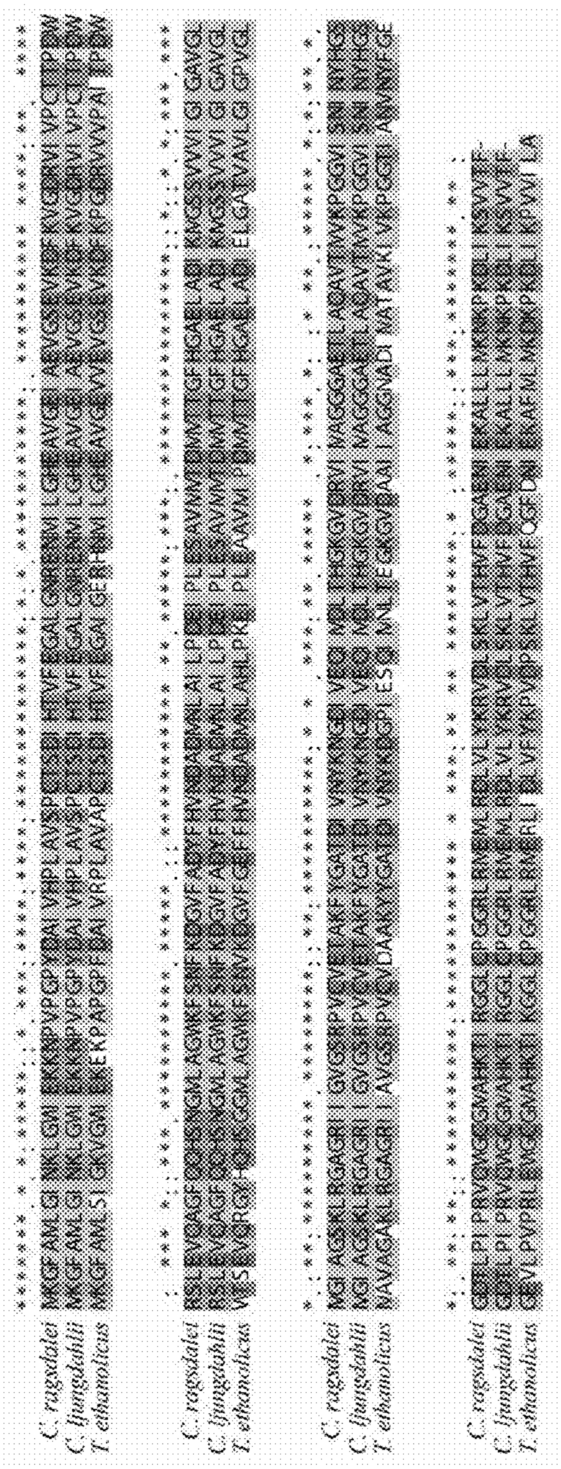
FIG. 4 is a diagram showing alignment of the genome architecture via the protein encoded by the gene for NADPH dependent secondary alcohol dehydrogenase in *C. ragsdalei* (SEQ ID NO:33), *C. ljungdahlii* (SEQ ID NO:34) and Thermoanaerobactor ethanolicus (SEQ ID NO:35), in accordance with the invention.

The genes encoding the NADPH-dependent secondary alcohol dehydrogenase (Gene ID 21, Table 1; Gene ID 19, Table 2) were sequenced in *C. ragsdalei* and *C. ljungdahlii.* Alignment 400 of the NADPH-dependent secondary alcohol dehydrogenase proteins of the acetogenic Clostridiae with the experimentally confirmed NADPH-dependent secondary alcohol dehydrogenase from *Thermoanaerobacter ethanolicus* are shown in FIG. 4. The *Thermoanaerobacter ethanolicus* NADPH-dependent alcohol dehydrogenase has been sequenced and purified. The anaerobic micro-organism is known to produce NADPH-dependent alcohol dehydrogenase activity having the amino acid sequence shown in FIG. 4. Coloration in alignment 400 indicates the degree of identity and similarity at each amino acid position in the three organisms. Asterisks indicate amino acids that are identical at the same position in all three organisms. Single dots above the amino acids indicate general similarity among the three proteins. Two dots indicate very similar amino acids among the three organisms. No dots or asterisks above the amino acids indicates no similarity. A high degree of gene conservation is observed for the NADPH-dependent secondary alcohol dehydrogenase enzyme in *C. ragsdalei* and *C. ljungdahlii.* Furthermore, in all three micro-organisms, the NADPH-dependent alcohol dehydrogenase exhibits a high degree of homology.

Key genes to modulate production of aliphatic $C_2$-$C_6$ alcohols and acids in *C. ragsdahlei* include:

SEQ ID NO 1 (ORF #RCCC02026, Table 1) the gene sequence for carbon monoxide dehydrogenase, cooS;

SEQ ID NO 2 (ORF #RCCC02027, Table 1), the gene sequence for electron transfer FeS protein cooF;

SEQ ID NO 3 (ORF #RCCC02028, Table 1), the gene sequence for the NADH dependent ferredoxin oxidoreductase (FOR);

SEQ ID NO 4 (ORF #RCCC01718, Gene ID 17, Table 1, FIG. 2, FIG. 5), the gene sequence for a phospho-transacetylase enzyme involved in acetate production;

SEQ ID NO 5 (ORF #RCCC01717, Gene ID 16, Table 1, FIG. 2, FIG. 5), the gene sequence for acetate kinase, an enzyme involved in acetate production;

SEQ ID NO 6 (ORF #RCCC02715, Gene ID 21, Table 1, FIG. 2, FIG. 5), the gene sequence for NADPH dependent secondary alcohol dehydrogenase;

SEQ ID NO 7 (ORF #RCCC01356, Gene ID 22, Table 1), the gene sequence for an adhE-type alcohol dehydrogenase;

SEQ ID NO 8 (ORF #RCCC01357, Gene ID 23, Table 1), the gene sequence for an adhE-type alcohol dehydrogenase;

SEQ ID NO 9 (ORF #RCCC01358, Gene ID 24, Table 1), the gene sequence for an adhE-type alcohol dehydrogenase, truncated;

SEQ ID NO 10 (ORF #RCCC03300, Gene ID 25, Table 1), the gene sequence for an iron-containing alcohol dehydrogenase;

SEQ ID NO 11 (ORF #RCCC03712, Gene ID 26, Table 1), the gene sequence for an iron-containing alcohol dehydrogenase;

SEQ ID NO 12 (ORF #RCCC04095, Gene ID 27, Table 1), the gene sequence for an iron-containing alcohol dehydrogenase;

SEQ ID NO 13 (ORF #RCCC0004, Gene ID 28, Table 1), the gene sequence for a short-chain alcohol dehydrogenase;

SEQ ID NO 14 (ORF #RCCC1567, Gene ID 29, Table 1), the gene sequence for a short-chain alcohol dehydrogenase;

SEQ ID NO 15 (ORF #RCCC2765, Gene ID 30, Table 1), the gene sequence for a short-chain alcohol dehydrogenase;

SEQ ID NO 16 (ORF RCCC2240, Gene ID 31, Table 1), the gene sequence for a short-chain alcohol dehydrogenase;

SEQ ID NO 17 (ORF #RCCC00020, Gene ID 18, Table 1), the gene sequence for an aldehyde ferredoxin oxidoreductase;

SEQ ID NO 18 (ORF #RCCC0030, Gene ID 19, Table 1), the gene sequence for an aldehyde ferredoxin oxidoreductase;

SEQ ID NO 19 (ORF #RCCC01183, Gene ID 20, Table 1), the gene sequence for an aldehyde ferredoxin ixidoreductase.

Key genes to modulate production of ethanol and acetate in *C. ljungdahlii* include:

SEQ ID NO 20 (ORF #RCCD00257, Gene ID 19, Table 2) the gene sequence for NADPH dependent secondary alcohol dehydrogenase;

SEQ ID NO 21 (ORF #RCCD00167, Gene ID 20, Table 2) the gene sequence for an adhE-type alcohol dehydrogenase;

SEQ ID NO 22 (ORF #RCCD00168, Gene ID 21, Table 2) the gene sequence for an adhE-type alcohol dehydrogenase;

SEQ ID NO 23 (ORF #RCCD02628, Gene ID 22, Table 2) the gene sequence for an adhE-type alcohol dehydrogenase;

SEQ ID NO 24 (ORF #RCCD03350, Gene ID 23, Table 2) the gene sequence for an adhE-type alcohol dehydrogenase;

SEQ ID NO 25 (ORF #RCCD00470, Gene ID 24, Table 2) the gene sequence for a short-chain alcohol dehydrogenase;

SEQ ID NO 26 (ORF #RCCD01665, Gene ID 25, Table 2) the gene sequence for a short-chain alcohol dehydrogenase;

SEQ ID NO 27 (ORF #RCCD01767, Gene ID 26, Table 2) the gene sequence for a short-chain alcohol dehydrogenase;

SEQ ID NO 28 (ORF #RCCD02864, Gene ID 27, Table 2) the gene sequence for a short-chain alcohol dehydrogenase;

SEQ ID NO 29 (ORF #RCCD01679, Gene ID 17, Table 2) the gene sequence for an aldehyde ferredoxin oxidoreductase; and SEQ ID NO 30 (ORF #RCCD01692, Gene ID 18, Table 2) the gene sequence for an aldehyde ferredoxin oxidoreductase.

Key genes to modulate production of butanol and butyrate in *C. carboxydivorans* include:

SEQ ID NO 31 (ORF #RCCB03972, Gene ID 84, Table 4, FIG. 8), the gene sequence for phosphate butyryltransferase; and SEQ ID NO 32 (ORF #RCCB03973, Gene ID 88, Table 4, FIG. 8), the gene sequence for butyrate kinase.

Using the detailed genomic information in Tables 1 through 4 and in the Sequence Listing, the acetogenic Clostridia micro-organisms have been metabolically engineered to increase the carbon and electron flux through the biosynthetic pathways for ethanol and butanol, while simultaneously reducing or eliminating carbon and electron flux through the corresponding acetate and butyrate formation pathways, in accordance with the present invention. For this purpose, the activities of key genes encoding for enzymes in the pathways have been modulated. In one embodiment, gene expression of key alcohol producing enzymes is increased (overexpression) by increasing the copy number of the gene. For example, a key carbon monoxide dehydrogenase operon (FIG. 3) and the associated electron transfer proteins, including NADPH-dependent secondary alcohol dehydrogenase (21, FIG. 2 and Table 1) and aldehyde ferredoxin oxidoreductase are duplicated within the genome of the modified organism. Alternatively, ethanol production can be increased by conversion of acetyl-CoA 102 first to acetaldehyde 604, then to ethanol 216 by overexpressing one or more of the other alcohol dehydrogenases present in the Clostridia micro-organisms' genome such as adhE-type alcohol dehydrogenase, iron-containing alcohol dehydrogenase, and short-chain alcohol dehydrogenases (21-31, Table 1; Gene ID 20-30, Table 2). In one embodiment, these duplications are introduced into strains having knocked out or attenuated acetate production to further channel electrons into the ethanol or butanol production pathway. In another embodiment a knockout strategy is applied to strains of acetogenic Clostridia that, when grown on syngas, produce more complex mixtures of alcohols and acids, such as ethanol, butanol and hexanol and their corresponding carboxylic acids.

In one embodiment, vectors to be used for the transfer of acetogenic Clostridia cloned genes from cloning vehicles to parent acetogenic Clostridia strains are constructed using standard methods (Sambrook et al., 1989). All gene targets used in molecular genetics experiments are amplified using high-fidelity polymerase chain reaction (PCR) techniques using sequence-specific primers. The amplified genes are next subcloned into intermediate cloning vehicles, and later recombined in multi-component ligation reactions to yield the desired recombinant vector to be used in the gene transfer experiments. The vectors contain the appropriate functional features required to carry out the gene transfer experiments successfully and vary depending on the method used.

To transfer the recombinant vectors into recipient acetogenic Clostridia, a variety of methods are used. These include electroporation, bi-parental or tri-parental conjugation, liposome-mediated transformation and polyethylene glycol-mediated transformation. Recombinant acetogenic Clostridia are isolated and confirmed through molecular biology techniques based on the acquisition of specific traits gained upon DNA integration.

Example 1

Acetogenic Clostridia contain operon 300, shown in FIG. 3, that consists of carbon monoxide dehydrogenase 104 (cooS, Gene ID 4, Table 1, Table 2, Table 3), a membrane-associated electron transfer protein (cooF), and a ferredoxin oxidoreductase (FOR). Overexpression of carbon monoxide dehydrogenase 104 within the acetogenic Clostridia is known to increase electron flow from syngas components to the oxidized nucleotide cofactors $NAD^+$ and $NADP^{+.}$ The increased levels of reduced nucleotide cofactors (NADH and NADPH) then stimulate generation of intermediate compounds in Wood-Ljungdahl pathway 100.

In one embodiment, operon 300 is amplified using long-PCR techniques with primers that are designed to anneal to a region 200 nucleotides (nt) upstream of the carbon monoxide dehydrogenase gene and 200 nt downstream of the ferredoxin oxidoreductase gene. The total region is about 3.8 kilobase pairs. The amplified DNA is cloned directly into suitable plasmid vectors specifically designed to ligate PCR products such as pGEM T easy (Promega, Madison, Wis.) or pTOPO (Invitrogen, Carlsbad, Calif.). The ends of the PCR product contain engineered restriction sites to facilitate later cloning steps. The operon 300 is subcloned into a vector that already contains cloned chromosomal *C. ragsdalei* or other acetogenic Clostridial DNA to allow chromosomal integration at a neutral site.

Example 2

Figure 5:
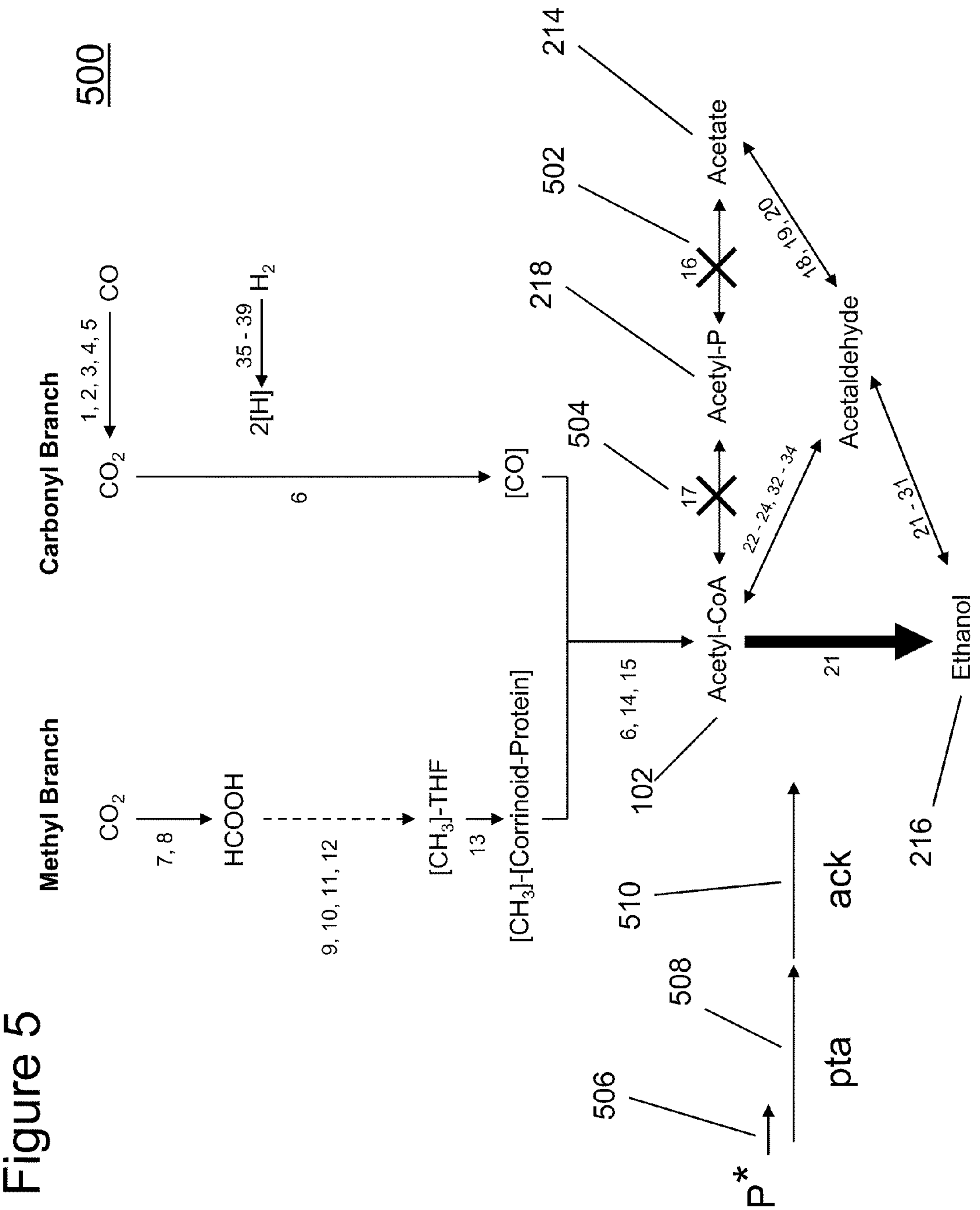
FIG. 5 is a diagram illustrating the Wood-Ljungdahl pathway for ethanol synthesis and showing a strategy for specifically attenuating or eliminating acetate production in acetogenic Clostridia by modifying (knocking out) the genes encoding acetate kinase (ack) and phosphotransacetylase (pta) or by modulating acetate production by mutating or replacing the promoter driving phosphotransacetylase and acetate kinase gene expression, in accordance with the invention.

Because carboxylic acids compete with alcohols for electrons, decreasing acid production allows more electrons to flow down the alcohol-production pathway from the CoA intermediate directly to the alcohol. Acetogenic Clostridia contain genes for phospho-transacetylase enzyme (Gene ID 17, Tables 1 and 3; Gene ID 16, Table 2) that converts acetyl-CoA 102 to acetyl-phosphate 218, and acetate kinase (Gene ID16, Table 1) that converts acetyl-phosphate 218 to acetate 214. In one embodiment, genetic modifications to delete all or part of the genes for both enzymes and knock out or attenuate production of acetate are made as shown in FIG. 5.

Using PCR and other standard methods, a recombinant vector containing two large non-contiguous segments of DNA is generated. Upon replacement of the native gene by the recombinant vector gene, the Clostridial strain contains no phoshotransacetylase or acetate kinase activities as shown in FIG. 5 by X 504 and X 502, respectively.

Modulation of the common promoter region, P* 506 to attenuate gene expression of phosphotransacetylase 508 and acetate kinase 510 and subsequent acetate production are carried out by generating a series of recombinant vectors with altered promoter regions. The vector series is constructed by site-directed mutagenesis.

Example 3

Figure 6:
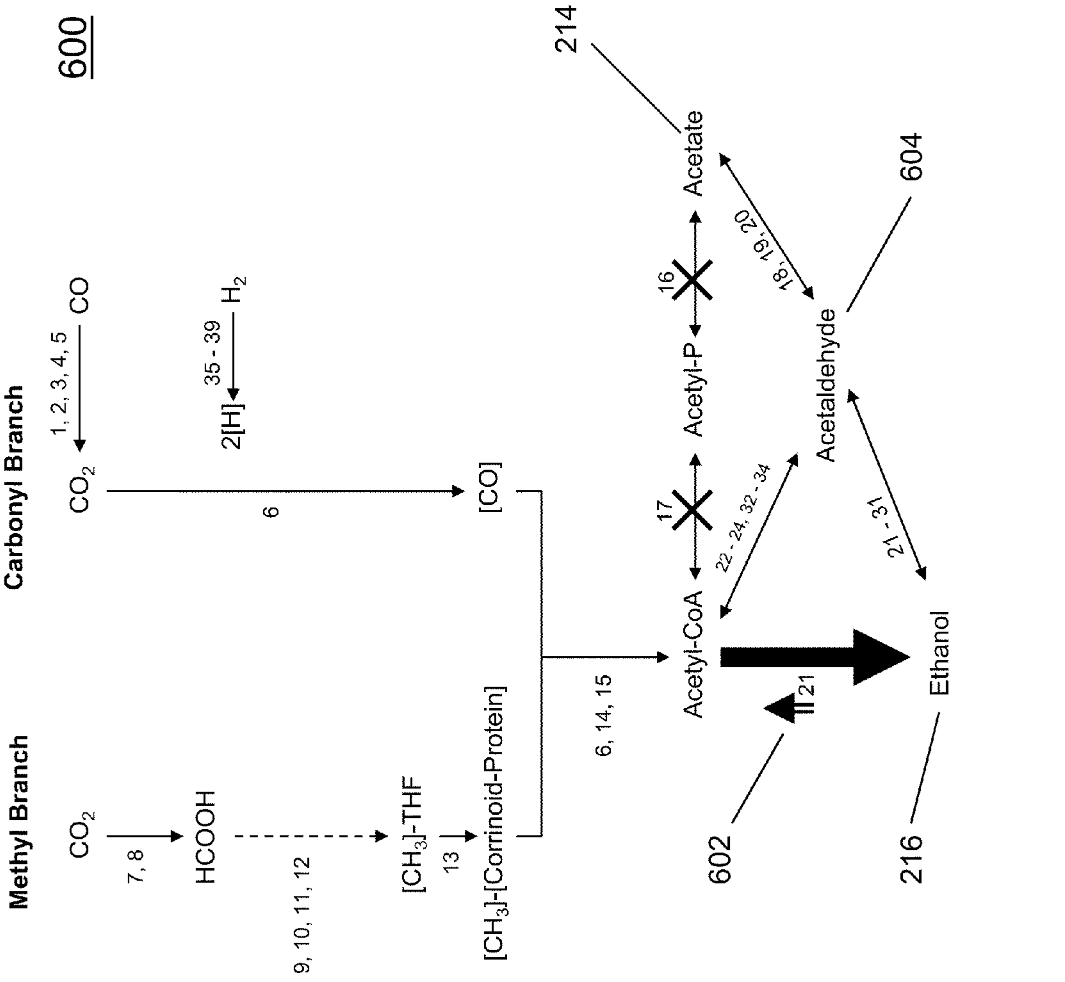
FIG. 6 is a diagram of the Wood-Ljungdahl pathway for ethanol synthesis, and showing a strategy for specifically increasing ethanol production in *C. ragsdahlei* by overexpression of a NADPH-dependent alcohol dehydrogenase in a host knocked out for acetate kinase or phosphotransacetylase activity, in accordance with the invention.

Secondary alcohol dehydrogenases are known to convert ketones to secondary alcohols. In vivo, the NADPH-dependent secondary alcohol dehydrogenase enzyme (Gene ID 21 in FIG. 5, Table 1, Gene ID 19, Table2) also converts the Coenzyme A (CoA) form of a carbon moiety, such as acetyl-CoA 102 or butyrl-CoA 806 (FIG. 8), directly to its corresponding alcohol. Thermodynamically, direct conversion from the CoA form to the alcohol requires transfer of four electrons, and is a more efficient way to generate the alcohol, compared to the two-step conversion of the carboxylic acid to the corresponding alcohol. For example, as shown in FIG. 6, the two step conversion requires that acetate 214, first be converted to its aldehyde form (acetaldehyde, 604), and then to the corresponding alcohol, ethanol 216. Thus, increasing secondary alcohol dehydrogenase activity, portrayed by the vertical arrow 602 is desirable for increasing alcohol production, and increasing the selectivity of the process by increasing the ratio of alcohol to acid.

In one embodiment, secondary alcohol dehydrogenase activity in acetogenic Clostridia is increased by amplifying the gene in vitro using high-fidelity PCR and inserting the duplicated copy of the gene into a neutral site in the chromosome using standard molecular genetic techniques. After gene replacement of the vector, the chromosome contains two copies of the secondary alcohol dehydrogenase. Confirmation of gene placement followed by gene expression studies of the recombinant strain are performed and compared to the parent strain.

In other embodiments a similar strategy is used to increase the enzymatic activity of adhE-type alcohol dehydrogenases, short-chain alcohol-dehydrogenases and primary Fe-containing alcohol dehydrogenases.

Example 4

Under some conditions, Clostridia need to obtain additional energy in the form of adenosine triphosphate production (ATP) causing the cells to temporarily increase the production of acetate 214 from acetyl-CoA 102. The net reaction is 1 ATP from ADP+$P_i$ through acetyl-phosphate. Acetate production is advantageous to the syngas fermentation process at low to moderate acetic acid concentrations, because it allows the cells to produce more energy and remain robust. However, too much free acetic acid causes dissipation of the transmembrane ion gradient used as the primary ATP generation source and therefore becomes detrimental to the cells. For industrial production purposes, it is advantageous to convert the acetate to ethanol to increase ethanol production and reduce the probability of accumulating too much free acetic acid.

Figure 7:
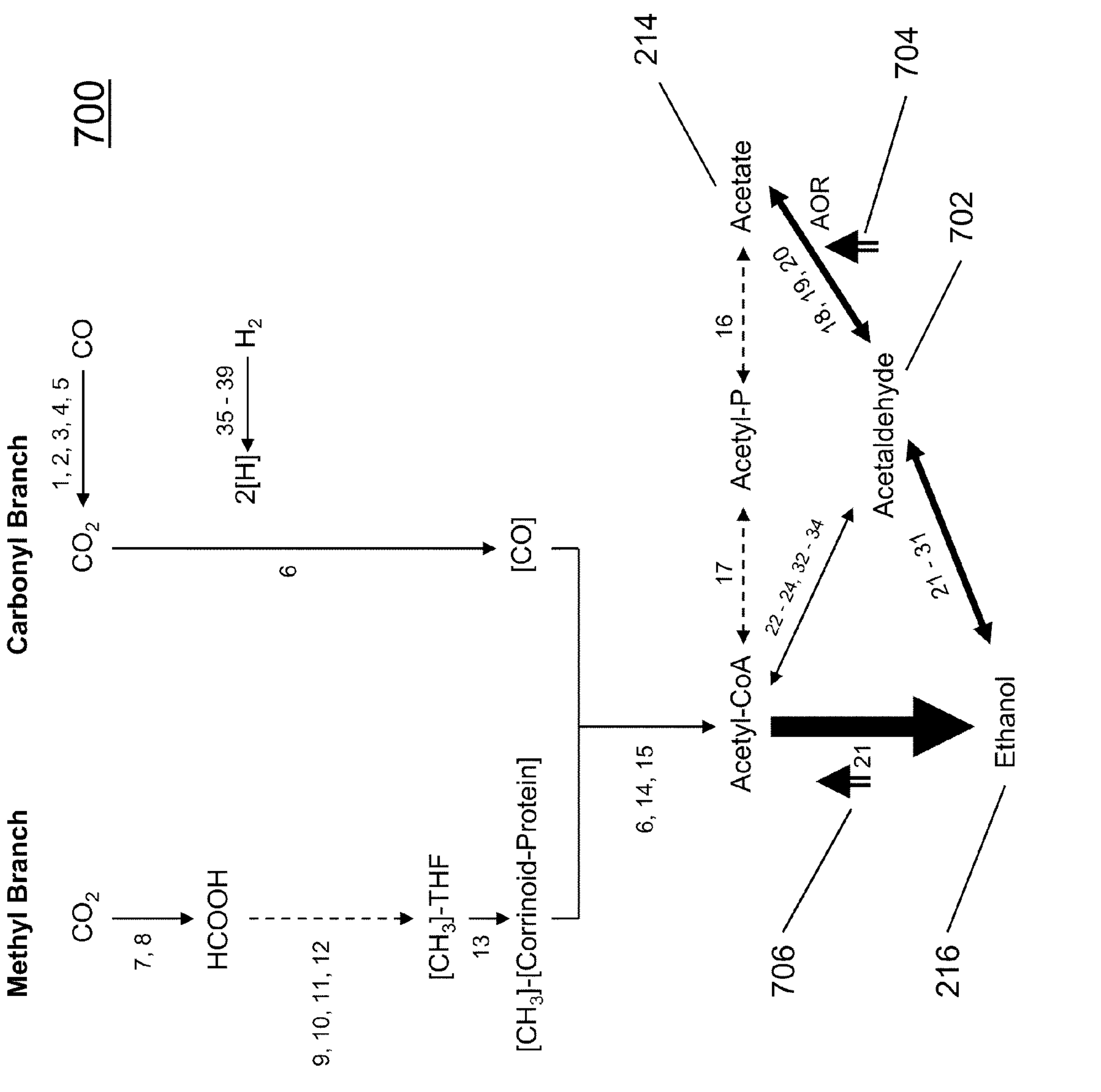
FIG. 7 is a diagram of the Wood-Ljungdahl pathway for ethanol synthesis, and showing a strategy for increasing ethanol production in acetogenic Clostridia by specifically increasing the conversion rate of acetate to ethanol through overexpression of aldehyde ferredoxin oxidoreductase (AOR) in a host strain that is attenuated in its ability to produce acetate and has increased NADPH-dependent alcohol dehydrogenase activity, in accordance with the invention.

Acetogenic Clostridia including, *C. ragsdahlei, C. ljungdahlii* and *C. carboxydivorans* contain the gene encoding the aldehyde ferredoxin oxidoreductase (Gene ID 18, 19, 20, Table 1; 17, 18, Table 2; and 18, Table 3) that converts acetate 214 to acetaldehyde. In one embodiment, the acetate-to-acetaldehyde conversion rate is increased in *C. ragsdahlei,* for example, as shown in FIG. 7. An aldehyde ferredoxin oxidoreductase (AOR) is duplicated in the genomes of *C. ragsdahlei* using methods described in several examples above. The gene is amplified and cloned into integration vectors containing acetogenic Clostridial DNA that allows insertion at a neutral site in the chromosome. Gene replacement strains are confirmed through standard molecular biological methods and acetate conversion rates will be determined using parent strains as controls. In one embodiment, acetate conversion is increased by between 10 and 20%, as indicated by vertical arrow 704.

In some cases, it is desirable to generate a double mutant through duplication of two genes to generate a strain that produces more ethanol through increased secondary alcohol dehydrogenase activity (21 Table 1; 19, Table 2) and also has improved acetate conversion capabilities. One embodiment of the invention, shown in FIG. 7, is dual mutant strain 700 of

*C. ragsdahlei.* This modified organism has elevated AOR activity, shown by vertical arrow 704 due to duplicated aldehyde ferredoxin oxidoreductase. The modified organism also has elevated NADPH dependent secondary alcohol dehydrogenase (21, Table 1 and FIG. 7) activity due to duplicated NADPH-dependent secondary alcohol dehydrogenase, indicated in FIG. 7 by vertical arrow 706.

In one embodiment, ethanol production in the double mutant *C. ragsdahlei* strain is increased by between 10 and 40% as a result of the increased AOR and NADPH-dependent secondary alcohol dehydrogenase activities. In another embodiment, the ratio of ethanol to acetate produced is increased between 5 and 10 fold, but allows sufficient acetate formation to support ATP production needed to meet the energy needs of the micro-organism.

Example 5

Figure 8:
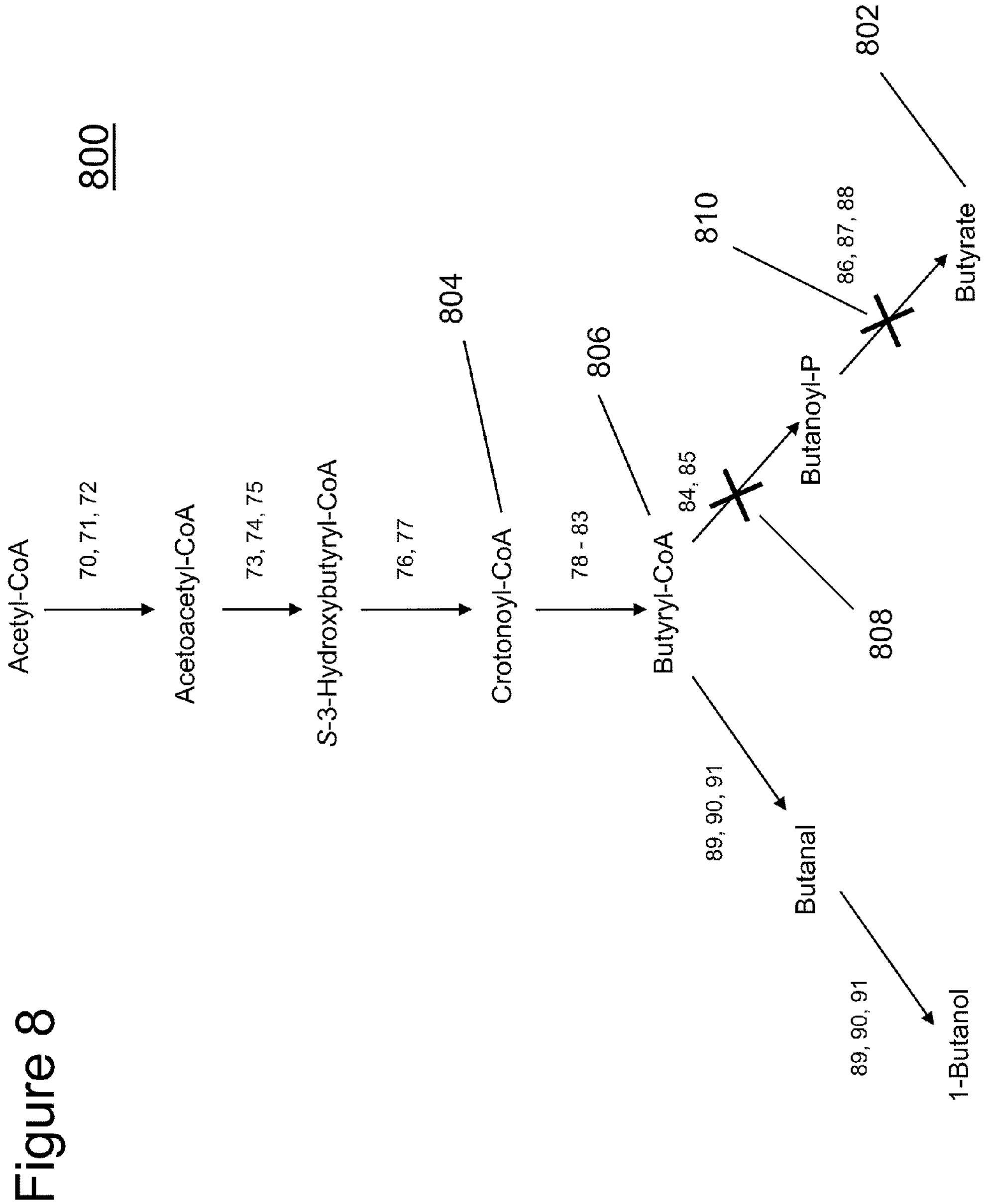
FIG. 8 is a diagram of the butanol and butyrate biosynthesis pathway in *C. carboxidivorans* and the corresponding genes catalyzing the conversion of acetyl-CoA to butanol and butyrate showing a strategy for increasing butanol production, in accordance with the invention.

Certain acetogenic Clostridia, *C. carboxydivorans* for example, produce significant amounts of $C_4$-$C_6$ alcohols and their corresponding acids in addition to ethanol and acetate. In some cases, a mix of alcohols is desirable for industrial production. As shown in FIG. 8, strategy 800, to be employed for increasing the production of $C_4$-$C_6$ alcohols in acetogenic Clostridia, is to block the strain's ability to produce butyrate 802 after the production of crotonyl-CoA 804. Similar to the phosphotransacetylase and acetate kinase operons identified in many acetogenic Clostridia, the genes for the conversion of butyryl-CoA 806 to butyrate 802 exist as one operon, comprising both phosphate butyryltransferase (Gene ID 84, 85, Table 4) and butyrate kinase (Gene ID 86, 87, 88, Table 4). The operon comprising the two butyrate production genes will be deleted from *C. carboxydivorans.* The desired recombinant strain will lack, or be attenuated in the transferase and kinase activities, as indicated by X 808 and X 810, respectively in FIG. 8.

While the invention has been described with reference to particular embodiments, it will be understood by one skilled in the art that variations and modifications may be made in form and detail without departing from the spirit and scope of the invention.

The invention claimed is:

1. A method for producing an aliphatic $C_2$, $C_4$, or $C_6$ alcohol comprising:

(a) providing an acetogenic *Clostridium* micro-organism having a genetic modification within at least one transcriptional unit, wherein the genetic modification substantially increases the expression of an NADPH-dependent secondary alcohol dehydrogenase gene as compared to the acetogenic *Clostridium* micro-organism without the genetic modification;

(b) supplying a syngas;

(c) culturing the acetogenic *Clostridium* micro-organism in a growth medium in the presence of the syngas;

(d) producing the aliphatic $C_2$, $C_4$, or $C_6$ alcohol by culturing the *Clostridium* micro-organism; and (e) recovering the aliphatic $C_2$, $C_4$, or $C_6$ alcohol produced in the culture.

2. The method of claim 1 wherein the aliphatic $C_2$, $C_4$, or $C_6$ alcohol is selected from the group consisting of ethanol, butanol, and hexanol.

3. The method of claim 1 wherein the acetogenic *Clostridium* micro-organism is selected from the group consisting of *Clostridium ragsdalei, Clostridium ljungdahlii, Clostridium carboxidivorans* and *Clostridium autoethanogenum.*

4. The method of claim 1 wherein the NADPH-dependent secondary alcohol dehydrogenase has the polynucleotide sequence of SEQ ID NO:20.

* * * * *

SEQUENCE LISTING

```
<160> NUMBER OF SEQ ID NOS: 35

<210> SEQ ID NO 1
<211> LENGTH: 1881
<212> TYPE: DNA
<213> ORGANISM: Clostriduim ragsdalei

<400> SEQUENCE: 1

atgtcaaata acaaaatttg taagtcagca gataaggtac ttgaaaagtt tataggttct     60

ctagatggtg tagaaacttc tcatcatagg gtagaaagcc aaagtgttaa atgtggtttt    120

ggtcagctag gagtctgctg tagactctgt gcaaacggtc cctgcagaat aacacctaaa    180

gctccaagag gagtatgtgg tgctagtgct gataccatgg ttgcaagaaa ctttcttaga    240

gctgtagctg ccggcagtgg atgttatatc catatagtcg aaaatacagc tagaaacgta    300

aaatcagtag gtgaaaccgg cggagagata aaaggaatga atgctctcaa caccctagca    360

gaaaaacttg gtataacaga atctgaccca cataaaaaag ctgtactagt agctgatgcc    420

gtattaaagg acttatacaa accaaaattc gaaaaaatgg aagttataaa taaattagct    480

tatgcaccta gactagaaaa ttggaacaaa ttaaatataa tgcctggcgg tgcaaaatca    540

gaagtttttg atggtgtagt aaaaacttct acaaatctaa acagcgaccc tgtagatatg    600

cttctaaatt gtttaaaact tggaatatcc actgggattt acggacttac ccttacaaat    660

ttattaaatg acataatttt aggtgaacct gctataagac ctgcaaaagt tggttttaaa    720

gttgtagata cggattatat aaatttgatg ataacaggcc accagcactc catgattgcc    780

caccttcaag aagaacttgt aaaacctgaa gctgtaaaaa aagcccaagc agttggtgct    840

aaaggattca aactagttgg atgtacctgt gtcggacagg atttacagtt aagaggtaaa    900

tactatactg atgttttctc cggtcatgca ggaaataact ttacaagtga agccttaata    960

gcaactggag gtatagatgc aatagtatct gaatttaact gtactcttcc tggcatcgag   1020

ccaatagctg ataagttcat ggttaaaatg atatgcctag atgacgtttc taaaaaatca   1080

aatgcagaat atgtagaata ctcttttaaa gatagagaaa aaataagcaa ccatgttata   1140

gatacggcta ttgaaagtta taaggaaaga agatctaaag ttacaatgaa tattcctaaa   1200

aaccatggct ttgatgacgt cataacaggt gtaagtgaag gttccttaaa atccttctta   1260
```

```
ggcggaagtt ggaaacctct tgtagactta attgctgctg gaaaaattaa aggtgttgct   1320

ggaatagtag gttgttcaaa cttaactgcc aaaggtcacg atgtatttac agtagaactt   1380

acaaaagaac tcataaagag aaatataatt gtactttctg caggttgttc aagtggtgga   1440

cttgaaaatg taggacttat gtctccagga gctgctgaac ttgcaggaga tagcttaaaa   1500

gaagtatgta agagcctagg tataccacct gtactaaatt ttggtccatg tcttgctatt   1560

ggaagattgg aaattgtagc aaaagaacta gcagaatacc taaaaataga tattccacag   1620

cttccacttg tgctttctgc acctcaatgg cttgaagaac aagcattggc agatggaagt   1680

tttggtcttg cccttggatt accacttcac cttgctatat ctcctttcat tggtggaagc   1740

aaagtggtaa caaaagtttt atgtgaagat atggaaaatc taacaggcgg caagcttata   1800

atagaagacg atgtaataaa agctgcagat aaattagaag aaaccatact tgcaagaagg   1860

aaaagcttag gtcttaatta a                                              1881
```

```
<210> SEQ ID NO 2
<211> LENGTH: 456
<212> TYPE: DNA
<213> ORGANISM: Clostriduim ragsdalei

<400> SEQUENCE: 2

atgaaaagaa taatgataaa taaggattta tgtaccggat gcttaaattg tactttagct     60

tgtatggcag aacacaatga aaatgggaaa tctttttatg atctggatct cagcaataaa    120

tttcttgaaa gtagaaatca tatatctaaa gatgataatg gaaacaagct tcctatattt    180

tgccgtcact gtgacgaacc tgagtgcgta atgacatgta tgagcggtgc catgactaaa    240

gatcctgaaa ctggtatagt atcctatgat gagcataaat gtgccagctg ctttatgtgc    300

gtcatgtcct gtccttatgg agtattgaaa ccagatactc agaccaaaag taaagtagtt    360

aaatgtgacc tgtgtggtga cagagataca cctagatgcg ttgaaaattg tccaacagaa    420

gcaatttata ttgaaaagga ggcagatctc ctatga                              456
```

```
<210> SEQ ID NO 3
<211> LENGTH: 1263
<212> TYPE: DNA
<213> ORGANISM: Clostriduim ragsdalei

<400> SEQUENCE: 3

atgagtggtt taacaataaa aatatttttt cacacaaaat atgtaataat aggagccagt     60

gctgctggaa taaatgctgc taaaacttta agaaagttag ataaatcctc caaaataact    120

attatttcaa aggatgatgc agtttattca agatgtatac tccacaaagt acttgaggga    180

agtagaaatt tagataccat aaattttgta gattctgatt tctttgaaaa aaataatata    240

gaatggataa aagatgcaga tgtaagcaat attgatattg acaagaaaaa agtcttactt    300

caagacaaca gcagcttcaa atttgacaag ctccttatag cttctggtgc ttcctccttt    360

attcccccag ttaaaaaatt aagagaagct aaaggagtgt actcccttag aaattttgaa    420

gatgtaactg ctatacaaga caaacttaaa aacgcaaaac aagtggtaat acttggtgca    480

ggtcttgtag gaattgatgc acttttaggt cttatggtga aaaatataaa gatttcagtt    540

gtagaaatgg gagataggat tctccccctt caactggaca aaactgcatc cactatatat    600

gaaaagttgt taaaagaaaa aggtatagat gtctttactt cagttaaatt ggaagaggta    660

gttttaaata aagacggaac tgtaagtaaa gcagtactat caaattcaac ttctatagat    720

tgcgatatga taatagttgc tgctggtgtt agaccaaatg taagctttat aaaagacagc    780
```

-continued

```
aggataaaag ttgaaaaagg cattgtcata gacaaacatt gtaaaaccac tgtagataat     840

atatatgctg caggagatgt tacttttact gctcctatat ggcctatagc tgtaaagcag     900

ggaataactg ctgcttacaa catggtaggt ataaatagag aattacatga cacttttggc     960

atgaagaact caatgaattt atttaacctt ccatgcgtat cccttggtaa tgtaaatata    1020

gcagatgaaa gttatgctgt tgatacatta gaaggagatg gagtttatca aaaaatagtt    1080

cacaaagatg gagtaatcta cggtgcactt ctagttggag atatatctta ctgcggcgta    1140

ctaggatatc tcataaaaaa taaagtaaat ataagcaata tccataaaaa tatttttgac    1200

atagattatt ctgattttta caatgttgaa gaagatggac aatatagtta tcaattgagg    1260

taa                                                                  1263
```

<210> SEQ ID NO 4
<211> LENGTH: 1002
<212> TYPE: DNA
<213> ORGANISM: Clostriduim ragsdalei

<400> SEQUENCE: 4

```
atgaaattga tggaaaaaat ttggaataag gcaaaggaag acaaaaaaaa gattgtctta      60

gctgaaggag aagaagaaag aactcttcaa gcttgtgaaa aaataattaa agaaggtatt     120

gcaaatttaa tccttgtagg gaatgaaaag gtaatagagg agaaggcatc aaaattaggc     180

gtaagtttaa atggagcaga aatagtagat ccagaaacct cggataaact aaaaaaatat     240

gcagatgctt tttatgaatt gagaaagaag aagggaataa caccagaaaa agcggataaa     300

atagtaagag atccaatata ttttgctacg atgatggtta agcttggaga tgcagatgga     360

ttggtttcag gtgcagtgca tactacaggt gatcttttga gaccaggact tcaaatagta     420

aagacagctc caggtacatc agtagtttcc agcacattta taatggaagt accaaattgt     480

gaatatggtg acaatggtgt acttctattt gctgattgtg ctgtaaatcc atgcccagat     540

agtgatcaat tggcttcaat tgcaataagt acagcagaaa ctgcaaagaa cttatgtgga     600

atggatccaa aagtagcaat gctttcattt tctactaagg gaagtgcaaa acacgaatta     660

gtagataaag ttagaaatgc tgtagaaatt gccaaaaaag ctaaaccaga tttaagtttg     720

gacggagaat tacaattaga tgcctctatc gtagaaaagg ttgcaagttt aaaggctcct     780

gaaagtgaag tagcaggaaa agcaaatgta cttgtatttc cagatctcca agcaggaaat     840

ataggttata aacttgttca aagatttgca aaagctgatg ctataggacc tgtatgccag     900

ggatttgcaa aacctataaa tgatttgtca agaggatgta actccgatga tatagtaaat     960

gtagtagctg taacagcagt tcaggcacaa gctcaaaagt aa                      1002
```

<210> SEQ ID NO 5
<211> LENGTH: 1197
<212> TYPE: DNA
<213> ORGANISM: Clostriduim ragsdalei

<400> SEQUENCE: 5

```
atgaaaatat tagtagtaaa ctgtggaagt tcatctttaa aatatcaact tattgatatg      60

aaagatgaaa gcgttgtggc aaaaggactt gtagaaagaa taggagcaga aggttcagtt     120

ttaacacata aagttaacgg agaaaagttt gttacagagc agccaatgga agatcataaa     180

gttgctatac aattagtatt aaatgctctt gtagataaaa aacatggtgt aataaaagat     240

atgtcagaaa tatctgctgt agggcataga gttttgcatg gtggaaaaaa atatgcggca     300

tccattctta ttgatgacaa tgtaatgaaa gcaatagaag aatgtattcc attaggacca     360
```

-continued

```
ttacataatc cagctaatat aatgggaata gatgcttgta aaaaactaat gccaaatact    420
ccaatggtag cagtatttga tacagcattt catcagacaa tgccagatta tgcttatact    480
tatgcaatac cttatgatat atctgaaaag tatgatatca gaaaatatgg ttttcatgga    540
acttctcata gattcgtttc aattgaagca gccaagttgt taaagaaaga tccaaaagat    600
cttaagctaa taacttgtca tttaggaaat ggagctagta tatgtgcagt aaaccaggga    660
aaagcagtag atacaactat gggacttact ccccttgcag gacttgtaat gggaactaga    720
tgtggtgata tagatccagc tataatacca tttgtaatga aagaacagg tatgtctgta    780
gatgaaatgg atactttaat gaacaaaaag tcaggaatac ttggagtatc aggagtaagc    840
agcgatttta gagatgtaga agaagctgca aattcaggaa atgatagagc aaaacttgca    900
ttaaatatgt attatcacaa agttaaatct ttcataggag cttatgttgc agttttaaat    960
ggagcagatg ctataatatt tacagcagga cttggagaaa attcagctac tagcagatct   1020
gctatatgta agggattaag ctattttgga attaaaatag atgaagaaaa gaataagaaa   1080
aggggagaag cactagaaat aagcacacct gattcaaaga taaaagtatt agtaattcct   1140
acaaatgaag aacttatgat agctagggat acaaaagaaa tagttgaaaa taaataa      1197
```

<210> SEQ ID NO 6
<211> LENGTH: 1056
<212> TYPE: DNA
<213> ORGANISM: Clostriduim ragsdalei

<400> SEQUENCE: 6

```
atgaaaggtt ttgcaatgtt aggtattaac aagttaggat ggattgaaaa gaaaaaccca     60
gtaccaggtc cttatgatgc gattgtacat cctctagctg tatccccatg tacatcagat    120
atacatacgg tttttgaagg agcacttggt aatagggaaa atatgatttt aggtcacgaa    180
gctgtaggtg aaatagctga agttggcagt gaagttaaag attttaaagt tggcgataga    240
gttatcgtac catgcacaac acctgactgg agatccttag aagtccaagc tggttttcaa    300
cagcattcaa acggtatgct tgcaggatgg aagttttcca attttaaaga cggtgtattt    360
gcagattact ttcatgtaaa cgatgcagat atgaatcttg caatacttcc agatgaaata    420
cctttagaaa gtgcagttat gatgacagac atgatgacta ctggttttca tggggcagaa    480
cttgctgaca taaaaatggg ttccagtgtt gtcgtaattg gtataggagc tgttggatta    540
atgggaatag ccggttccaa acttcgagga gcaggtagaa ttatcggtgt tggaagcaga    600
cccgtttgtg ttgaaacagc taaattttat ggagcaactg atattgtaaa ttataaaaat    660
ggtgatatag ttgaacaaat aatggactta actcatggta aaggtgtaga ccgtgtaatc    720
atggcaggcg gtggtgctga aacactagca caagcagtaa ctatggttaa acctggcggc    780
gtaatttcta acatcaacta ccatggaagc ggtgatactt tgccaatacc tcgtgttcaa    840
tggggctgcg gcatggctca caaaactata agaggagggt tatgtcccgg cggacgtctt    900
agaatggaaa tgctaagaga ccttgttcta tataaacgtg ttgatttgag caaacttgtt    960
actcatgtat ttgatggtgc agaaaatatt gaaaaggccc ttttgcttat gaaaaataag   1020
ccaaaagatt taattaaatc agtagttaca ttctaa                             1056
```

<210> SEQ ID NO 7
<211> LENGTH: 2712
<212> TYPE: DNA
<213> ORGANISM: Clostriduim ragsdalei

<400> SEQUENCE: 7

-continued

```
gtggagttaa aactccatct gatgccaaga aatctgttta tatttaacag catgaaaaat     60
aagaaagagg tgtcattaat gaaggtaact aaggtaacta acgttgaaga attaatgaaa    120
aagttagatg aagtaacggc tgctcaaaaa aaattctcta gttatagtca ggaacaagtg    180
gatgagatct ttaggcaggc agctatggca gccaatagtg ctagaataga tctagctaaa    240
atggcagtgg aagaaagcgg aatgggaatt gtagaagaca aggttattaa aaatcatttt    300
gtttcagaat atatatataa caaatataag gatgaaaaga cctgtggagt tttagaagaa    360
gaccaaggtt ttggtatggt tagaattgcg gaacctgtag ggttatagc agcagtagtt    420
ccaacaacta atccaacatc cacagcaatc tttaaatctt taatagcttt gaaaactaga    480
aatggtatag tttttttcacc acatccaaga gcaaaaaaat caactattgc agcagctaag    540
atagtacttg atgcagcagt taaagctggt gctcctgaag gaattatagg atggatagat    600
gaaccttcca ttgaactctc acaggtggta atgaaagaag cagatttaat tcttgcaact    660
ggtggcccgg gtatggttaa ggctgcctat tcttcaggaa agcctgctat aggagttggc    720
ccaggtaaca cacctgctgt aattgatgaa agtgctgata ttaaaatggc agtaaattca    780
atactccttt caaaaacttt tgataatggt atgatttgtg cttcagagca gtcagtagta    840
gttgtaagct caatatacga tgaagtcaag aaagaatttg cagatagagg agcgtatata    900
ttaagtaagg atgaaacaga taaggttgga aaaacaatta tgattaatgg cgctctaaat    960
gctggcattg tagggcaaag tgcttttaaa atagcacaga tggcaggagt gagtgtacca   1020
gaggatgcta aagtacttat aggagaagtt aaatcagtag aacctgaaga agagcccttt   1080
gctcatgaaa agctgtctcc agttttagct atgtacaaag caaaagattt tgatgaagca   1140
cttctaaagg ctggaagatt agttgaacga ggtggaattg ggcatacatc tgtattatat   1200
gtaaattcaa tgacggaaaa agtaaaagta gaaaagttca gagaaactat gaagactggt   1260
agaacattga taaatatgcc ttcagcacaa ggtgctatag gagatatata taactttaaa   1320
ctagctcctt ctttgacgct aggatgtggt tcctggggag gaaactctgt atcagaaaat   1380
gttggaccta aacatttatt aaacataaaa agtgttgctg agaggagaga aaatatgctt   1440
tggtttagag tacctgaaaa agtttatttc aaatatggta gtcttggagt tgcattaaag   1500
gaattgagaa ctttggagaa gaaaaaggca tttatagtaa cggataaggt tctttatcaa   1560
ttaggttatg tagataaaat tacaaaaaat ctcgatgaat taagagtttc atataaaata   1620
tttacagatg tagaaccaga tccaaccctt gctacagcta aaaaaggtgc atcagaactg   1680
ctttcctatg aaccagatac aattatagca gttggtggtg gttcggcaat ggatgcagcc   1740
aagatcatgt gggtaatgta tgagcatcca gaagtaagat ttgaagattt ggctatgaga   1800
tttatggata taagaaagag agtatatgtt tttcctaaga tgggtgaaaa agcaatgatg   1860
atttcagtag caacatccgc aggaacagga tctgaagtta ctccatttgc agtaattacg   1920
gatgaaagaa caggagctaa atatccactg gctgattatg aattgactcc aaacatggct   1980
ataattgatg cagaacttat gatgggaatg ccaaaagggc ttacagcagc ttcgggtata   2040
gatgcattaa cccatgcact ggaggcgtat gtatcaataa tggcttcaga atataccaat   2100
ggattggctc ttgaagcaac aagattagta tttaaatatt tgccaatagc ttatacagaa   2160
ggtacaacta atgtaaaggc aagagaaaaa atggctcatg cttcaactat agcaggtatg   2220
gcttttgcca atgcattctt aggggtatgt cactctatgg cacataaatt gggagcacag   2280
caccatatac cacatggaat tgccaatgcg cttatgatag atgaagttat aaaattcaat   2340
gctgtagagg ctccaaggaa acaagcggca tttccacaat ataagtaccc aaatgttaaa   2400
```

-continued agaagatatg ctagaatagc tgattactta aatttaggag gaagcacaga tgatgaaaaa 2460
gtacaattgc taataaatgc tatagatgac ttaaaaacta agttaaatat tccaaagact 2520
attaaagagg caggagtttc agaagataaa ttctatgcta ctttagacac aatgtcagaa 2580
ctggcttttg atgatcaatg tacaggagct aatccaagat atccactaat aggagaaata 2640
aaacaaatgt atataaatgc atttgataca ccaaaggcaa ctgtggagaa gaaaacaaaa 2700
aagaaaaaat aa 2712

<210> SEQ ID NO 8
<211> LENGTH: 2400
<212> TYPE: DNA
<213> ORGANISM: Clostriduim ragsdalei

<400> SEQUENCE: 8
ttgcctcaga atatatataa caaatataag gatgaaaaga cctgtggagt tttagaaaga 60
gatgcaggct ttggtatagt tagaattgcg gaacctgtag ggttattgc agcagtagtt 120 ccaacaacta atccaacatc tacagcaatc tttaaatcac taatagcttt aaaaactaga 180
aatggtataa ttttttcacc gcatccaagg gcaaagaaat caactattgc agcagctaaa 240
atagtacttg atgctgcagt taaagctggt gctcccgaag gaattatagg atggatagat 300
gaaccttcca ttgaactttc acaggtggta atgggagaag caaatttaat tcttgcaact 360
ggtggcccgg gtatggttaa ggctgcctat tcttcaggaa aacctgctgt aggagttggc 420
ctaggtaata cacctgctat aattgatgaa agtgccgata ttaaaatggc agtaaattca 480
atattactct caaaaacttt tgataatggt atgatttgtg cctcagagca gtcagtaata 540
gttttagact caatatatga ggaagttaaa aaagaatttg cttatagggg agcttatata 600
ttgagtgagg atgaaacaga taaggttgga aaaataattt taaaaaatgg agccttaaat 660
gctggtattg taggacaaag tgcttttaaa atagcacagc tggcaggagt gaacgtacca 720
gaaaaagcta aagtacttat aggagaggta gaatcagtag aacttgaaga accattttct 780
catgaaaagt tatctccagt tttagctatg tacagggcaa gagattttga ggatgccatt 840
gcaaaaactg ataaactggt tagggcaggt ggatttggac atacatcttc attatatgta 900
aatccaatga cagaaaaagc aaaagtagaa aaatttagta ctatgatgaa aacatcaaga 960
actataatta acacaccttc atctcaaggt ggtataggtg acatatataa ctttaagcta 1020
gctccttcgc tgacgctagg ctgcggatct tggggaggaa actctgtatc cgaaaatgtt 1080
gggcctaaac atttattaaa cataaaaagt gttgctgaga ggagagaaaa tatgctttgg 1140
tttagagtgc ctgaaaaggt ttatttcaaa tacggtagtc ttggagttgc attaaaagaa 1200
ttaaaagtta tgaataagaa gaaagtattt atagtaacag ataaagtcct ttatcaatta 1260
ggttatgtgg acaaagttac aaaagttctt gaggaactaa aaatttccta taaagtattt 1320
acagatgtag aaccagatcc aacccttgct acagctaaaa aaggtgcagc agaattgctg 1380
tcatatgaac cggatacaat tatatcagtt ggtggtggtt cagcaatgga tgcagccaag 1440
attatgtggg taatgtatga gcatccagaa gtaaaatttg aagatttagc tatgagattt 1500
atggatataa gaaagagagt atatgttttc cctaagatgg gagaaaaagc aatgatgatt 1560
tcagtagcaa catccgcagg tacaggatca gaagttactc catttgcagt aattacagat 1620
gaaaaaacag gagctaaata tccattagct gattatgagt taactccaaa catggctata 1680
gttgatgcag aacttatgat gggaatgcca agaggactta cggcagcgtc aggtatagat 1740
gcattaactc atgcactgga agcttatgta tcaataatgg ctacagaatt taccaatgga 1800

```
ttagcccttg aagcagtaaa gttgatattt gaatatttac caaaagctta tacagaaggt   1860
acaactaatg taaaggcaag agaaaaaatg gctcatgctt catgtattgc tggtatggct   1920
tttgcaaatg cattcttagg ggtatgccac tctatggcac ataaattagg agcacagcac   1980
cacataccac atggaattgc taatgcactt atgatagatg aagttataaa attcaatgct   2040
gtagatgatc caataaaaca agctgcattt cctcaatacg agtatccaaa tgccaagtat   2100
agatatgctc agatagctga ttgtctcaac ttaggaggaa atacagaaga tgaaaaggtg   2160
caattattaa taaatgctat agatgatcta aaagctaagt taaatattcc agaaacgatt   2220
aaagaagcag gagtttcaga agaaaaattc tatactactt tagataaaat gtcagaatta   2280
gcttttgatg atcaatgtac aggagctaac ccaaggtatc cactaataag tgaaataaaa   2340
caaatgtata taaatgtttt tgataaaact gaaccaattg tagaagatga agaaaagtaa   2400
```

<210> SEQ ID NO 9
<211> LENGTH: 231
<212> TYPE: DNA
<213> ORGANISM: Clostriduim ragsdalei

<400> SEQUENCE: 9

```
atgaaagtta caaacgtgga agaattaatg aaaagactag aagagataaa ggatgctcaa     60
aagaaatttg ctacatatac tcaagaacaa gtggatgaaa tttttagaca agcagctatg    120
gcagccaata gtgctagaat agaactagct aaaatggcag tggaagaaag cggaatggga    180
attgtagaag acaaggttat taaaaatcac tttgcctcag aatatatata a             231
```

<210> SEQ ID NO 10
<211> LENGTH: 1173
<212> TYPE: DNA
<213> ORGANISM: Clostriduim ragsdalei

<400> SEQUENCE: 10

```
atgattattg tgaaaaattt taatgttaaa ccaaaggttt attttggtac tgatgcttta     60
aatcatttgt gtgaattaaa atgtaagaaa gctttaatcg ctgcagatcc atttatggtt    120
aagtcatcaa cggttgataa aattactgaa cagcttgata aggcacatat agagtatgat    180
atattttcag atatagtacc agatcctcct gttgaagtta ttataaaagg agtgcaggaa    240
gctgttaaat ttaaacctga tgtacttata gcacttggag gaggatcagc tattgattct    300
gcaaaaggaa taaggtattt ttgtcagtat gtaaataatg aattgaataa cgaaatgaaa    360
gagcccctgt ttatagcaat tccgacaaca agtggtacag gctctgaggt tactaacttt    420
tgtattgtaa ctgataagca aaaaggagtc aaatatgctc ttgttgatga caatttgacg    480
ccggatcagg cggtacttga tattgaactt gtaaaatcag tgccaaaagc taccacatca    540
gaaacaggaa tagacgtact tacacatgga attgaagcat atgtttctac aaatagatca    600
gattattctg atgcactggc agaaaaatca ataaaaaatgg tatttaaata cttgttagcc    660
gcatatgaaa atggagatga tgaagaagct agaacgaaga tgcataatgc atcctgcata    720
gcaggtatgg catttacaaa tgcttccctt ggacttaacc atggcatggc tcatgcactt    780
ggtggaaaaa ttcatatacc gcatggaaga gcaaatggac tacttcttcc atacgtaata    840
gagtataatg caaaccttaa aaacttacaa ggaaagataa accattctag tgcagcatat    900
aggtatactg aaatatcaaa attcttggga cttccagcat ctaaccaatt tgaaggtgtt    960
aggagtttga ttgcagcagt taagatactg atgaataaac ttaacttacc taaatgtatt   1020
aataattgtg aagttttatg tgaaaatttg gataatgaga ttcatgagtt atcgataact   1080
```

-continued gccctaaatg atagatgtac aaaaacaaat ccgagaattc ctgaaataaa ggatgttgaa 1140
aatttgttta agagggtttt ttctaaagaa taa 1173

<210> SEQ ID NO 11
<211> LENGTH: 1146
<212> TYPE: DNA
<213> ORGANISM: Clostriduim ragsdalei

<400> SEQUENCE: 11
atggattatt cagtttttca aagtcccaag aaaataatgt atggaaaaaa taccgcaaat 60
ttcattggaa atgaagcagc ggtgtttgga aataaggcaa tgatagttac aggaaaacat 120
tcatcaaaaa agacaggtgc attagataaa gtttactata gtttaaaaga tcagggaata 180
gatcctgtta tatttaataa agtagaatca gatcctagtg tttttactgt aagggaagga 240
gtgaaagtag gaaaagaaga aaaagtagat tttatagttg ccttaggtgg aggaagtgct 300
atggatgcag ccaaagccat aagtatggtt ataggaaatg gaggggatat tttagattat 360
gaaaaagttc agcctaaaac ttatggaata cctattatag cagttcctac tacagcagga 420
actggaagtg aagttagtaa gttttctata ataacagata ctgaaagaaa gataaagatg 480
cttatttcaa gtaactttat aatacctgaa atagcaattt tagatccact tttgactatg 540
atgatgccgc ctcaagttac ggcagctaca gggatggatg ctttcactca tgcaattgag 600
gcatatattt caaaggctgc acagccaatg tcagatacat ttgcaataaa ggcaataaat 660
gttataagca gtaatatttc acggtcagtg cttaaaggtg atattgaagc cagagaaaaa 720
atgttgcttg gacagatgta tgcaggactt gcttttagca atgcatctac agcacttgtt 780
cattcaatgt caagaccttt aggagcttac tataaagttc cccatggaat ggcaaatgca 840
attttgctta cagaggttat gaaatttaat agagcttctt gtgctgaaag atttaaagtt 900
atagcggaag ctatgggaga aaatgtagaa ggaaaatctg taagagaggc aagcttgatt 960
gcagtagata ctataaggtc tattttcttg gaaacaggac ttccagtatc acttaaagaa 1020
gttggtgtag acaaagacaa ttttagaaag atggcagaag atgctatgga aagcaaaact 1080
acagctctta atccgagaaa acctacacta gagcagttag tagaaatata tgaaaagata 1140
tattaa 1146

<210> SEQ ID NO 12
<211> LENGTH: 1149
<212> TYPE: DNA
<213> ORGANISM: Clostriduim ragsdalei

<400> SEQUENCE: 12
atggaagaca agtttgaaaa ttttaatttg aaatccaaga tttattttaa tagggaatcc 60
atacaacttt tagagcaggt tactggctct cgagcattta ttgttgcaga tgccattatg 120
ggaaaacttg gatatcttca aaaagtaata gattccctaa gtaaagccgg aataagttcc 180
gttgttttta cgggagtaca ccctgatcca gatgtcaatg taattgcaga tgcaatgaaa 240
ttgtacaaca aaagcgatgc agatgttctc gttgcactag gtggaggctc cagcattgat 300
accgccaaag gaataatgta ttttgcatgt aatttaggaa aagcaatggg ccaggaaatg 360
aaaaagcccc tgtttattgc aattccatca acaagtggaa caggctctga agtaacaaac 420
tttactgtta ttacttctca gaaagaaaag gtatgcattg tagatgattt tattgcacca 480
gacgttgcaa tacttgactc tagttgtatt gatggtctgc ctcaacgtat tgtagcagat 540
actggtatag atgttctagt tcattctatt gaagcctatg tttccaaaaa agcaactgac 600

```
tttacagacg ctcttgctga aaaagcagtt aaattgattt ttgagaatct tccaaaaatt    660

tataacgata gtaaagattc tgaagctcga gatcatgttc aaaacgcttc ttgtatagca    720

ggaatagcat ttacaaatgc tggtcttgga attaatcaca gcttggctca tgctatgggt    780

ggatcttttc acattcctca cggccgatcc aatgcacttt tacttaatgc agtaatggaa    840

tacaatgcta gcttagtggg aaatgcaaac gatcatgcta tggaaaaata cgcaaaacta    900

gcatcagttc tacaccttcc agctcgaaca actcgtgaag gcgctgtaag ttttatcgaa    960

gctgtaaata aattaataaa atccctaggt gttgaagata atattcgagc tcttggaatt   1020

aaagaagacg attttcaagg tgctctaaat catatggcag aaacagcaat gcaagataga   1080

tgcactccaa ctaatcctag aaaaccttct aaagaagaac tgatacatat ttatcaaaaa   1140

tgctattaa                                                          1149
```

<210> SEQ ID NO 13
<211> LENGTH: 867
<212> TYPE: DNA
<213> ORGANISM: Clostriduim ragsdalei

<400> SEQUENCE: 13

```
atgaatttc caacatcttt tccaaagcag catcagaatc atcatccggg atttcagtat     60

gaaatgaatc ctatgcctat atgtgatgat gctgtgtata atagaaaagg agacctttta    120

aaaggaaaaa ctgccataat tacaggtggt gacagcggta taggtagagc tgtttctata    180

gcttatgcga accaaggtgc agatgtagta attgtatact taaatgaaca aaaagatgct    240

gaggaagcta aaagacttgt agaaagtaag ggaacaaagt gcacacttat agcagggaat    300

attagtgatg taaatttttg caatagcgtt gtagaaaaaa ctataagcga atatggaaaa    360

atagacatac tagttaataa tgctgctgtc caatatgaat gtactgatat aaagcagtta    420

tcagatgaac aatttgacag aacttttaaa accaatgcat acggaacttt ctatatgaca    480

agggcagcaa tgaatcactt aaaatcagga gcatgcataa taaatacagc ttctatagta    540

gcttttaaag gaagtgctac gctcatagat tattccatga caaaaggtgc aatagtagct    600

tttactagat cattatctac tgcacttgca aaagggaaga ctggaataag ggtaaatgca    660

gttgcaccag ggccaatttg gacacctctt ataccatctt gttttgatga aacaaaaact    720

tcccagtttg gaggggatac tccaatggca agagcagggc agcctgtgga atgtgcagga    780

acttatgtat ttttagcttc tgaaaacgcc tcttatatta cgggtcagac tatccgtgta    840

aatggaggag aagtagtgaa cggttga                                       867
```

<210> SEQ ID NO 14
<211> LENGTH: 846
<212> TYPE: DNA
<213> ORGANISM: Clostriduim ragsdalei

<400> SEQUENCE: 14

```
gtgatttatg atgtagttaa tttttattac tggaggttaa ttgttatgaa aaatgaaata     60

gttgttttaa ttactggatg ttctacaggg attggaagag agctttgtag tatattgttt    120

cacaaaggat gtacggttgt tgcaacagca agaaatgtag aaactttaaa agatttatct    180

gcgtccttaa gattaccact ggatgttacc caaaaagagt ctattaacag tacaataaat    240

gaagttgtat caaaatttca taaaattgat attcttataa ataacgcagg ctattcaatt    300

agaggagctt tagaagaaat tgatttaaat agtgctaaaa gtatgtttga tgtaaatgta    360

tttggtatta ttaacatgat tcaggcagtt attccagaaa tgcgtaaaaa acaatttggt    420
```

-continued

```
aagattataa atattggctc catttcaggg aaatttgttc aatccatcaa tggagcgtat    480

tgtgcatcaa aatttgcagt tgaggcacta agtgacacac ttcgtttaga attacacagc    540

tacaatattc agagcaccgt cattgagcca ggtcccatga aaaccaactt ttttaaggca    600

ttagtggata attcaggcga tgttataaaa aatgaaaatt cttgttattc acatttttat    660

aaatcagatg atgaatatag aaaaaagcaa aaacaagctg atcctaaagt agcagcacaa    720

gctattagtg atataatttt gaaaaaacga cttaatgctc gttataaagt tgctgttcca    780

tttacatata agatggttac atattttcct gattttctaa gagaatactt tatgaaaaaa    840

agatag                                                               846
```

<210> SEQ ID NO 15
<211> LENGTH: 873
<212> TYPE: DNA
<213> ORGANISM: Clostriduim ragsdalei

<400> SEQUENCE: 15

```
atgtgttcaa atcatattgg atgcaaattt ccacgctttt ttccacccca acatcagcca     60

catcaacctg gtattgaata tattatgaca cctagaccag ttttcgaacc accattatgt    120

gcacaatatc aaacgacaaa aagattatta aacaaagtag ctttaataac aggaggagac    180

agcggtattg ggcgtgctgt agcatgtgct tatgcaaaag aaggagctga tattgccatt    240

gtctatctaa atgaacatgt agatgcagag ggaacaaaat ctagaataaa aaaattgggg    300

cgaagatgtt taaccattcc aattaacata ggagtcgaag agaatagtaa aattataatt    360

caagaagtta tgaatcattt tggtaaatta gatattcttg taaataatgc tgcagtactt    420

tattacaata attctataga agaagtatct agcaaacaat tagaatggac ttttcgtata    480

aatgtatttt cttatttcta cttaactaaa gcagctctac cttatatgaa accaggcggt    540

tctatcatca atacttcttc aatagttgct tttaatcctc cttatgggat atctttagat    600

tatgaagctt caaaaggtgc cattgctaat ttcactataa atttagcccg aagtttggtt    660

tcaagaggaa tacgtgtaaa tggtgtagct ccaggtgaaa cctggacacc tttaattcca    720

gcaggattac ctgcagataa agttgccgtt tggggttcaa aaacaccaat gggaagagct    780

gctcaaccat ttgaaattgc tccagcctat gtattcttag cttccaatga atcaagctat    840

atgtcaggac aaacaatcca tatgtattct taa                                 873
```

<210> SEQ ID NO 16
<211> LENGTH: 789
<212> TYPE: DNA
<213> ORGANISM: Clostriduim ragsdalei

<400> SEQUENCE: 16

```
atgactttaa ctaatgaaaa gactgttcta attacaggag cttcaaacgg aataggactt     60

gagcttgcaa aactattttc taaggatggg tataatttaa tacttgtagc tagaagtgaa    120

aacaaattag tagaaatagc aaaaaattta ataaaaaaat ataatattaa tgtacatata    180

ataaaagaag atctttcaaa aaaagaatct gtaaaagatc tatttttgaa agtacaacaa    240

ctaggcataa gggtaactac tcttgttaat aatgcaggta caggttactg tggacttttt    300

catgaaattg atatagacaa agatgaagaa atgatagggt taaacattga agctattact    360

tatttaacga aattattttc aaaagagatg ataaagttaa aaaaggggag tatattaaat    420

gtggcatcta cgggttctta tgaaccagga ccttatactg cagtatatta tgcctctaaa    480

gcatatgtac tatccttttc tcaagccctt gaaaatgagc taaagccata tggcataaaa    540
```

-continued gtatgtactc tgtgcccggg agctactaaa actggatttt ctaaaaatgc aggtaaaaaa 600
gatatgaaaa ctgctatgag tgctgaaaaa actgctgaga tagcttatat aggatttatg 660
aaaaataaat ctattataat accaggattt tttaataaaa tagctgtttt attttgtaag 720
ctattgccag gcaaaatttc tgcggtcatt gttagaaaaa tacaggaaaa ggcaactaaa 780
aatttttaa 789

<210> SEQ ID NO 17
<211> LENGTH: 1824
<212> TYPE: DNA
<213> ORGANISM: Clostriduim ragsdalei

<400> SEQUENCE: 17
atgtatggtt ataatggtaa agtattaaga attaatttaa aagaaagaac ttgcaaatca 60
gaaaatttag atttagataa agctaaaaag tttataggct gtaggggact aggtgttaaa 120
actttatttg atgaaataga tcctaaaata gatgcattat caccagaaaa taaatttata 180
attgtaacag gtccgttaac tggagctcca gttccaacta gtggaaggtt tatggtagtt 240
actaaagcac cgcttacagg aactatagga atttcaaatt cgggtggaaa atggggagta 300
gacttgaaaa aagctggctg ggatatgata atagtagagg ataaggctga ttcaccagtt 360
tacattgaaa tagtagatga taaagtagaa attaaagatg cgtcacagct ttggggaaaa 420
gttacatcag aaactacaaa agagttagaa aagataactg agaatagatc aaaggtatta 480
tgtataggac ctgctggtga aagattgtcc cttatggcag cagttatgaa tgatgtagat 540
agaactgcag caagaggcgg cgttggtgca gttatgggat ctaaaaactt aaaagctatt 600
acagttaaag gaactggaaa aatagcttta gctgataaag aaaaagtaaa aaaagtgtcc 660
gtagaaaaaa ttacaacatt aaaaaatgat ccagtagctg gtcagggaat gccaacttat 720
ggtacagcta tactggttaa tataataaat gaaaatggag ttcatcctgt aaataatttt 780
caagaatctt atacggatca agcagataaa ataagtggag agactcttac tgctaaccaa 840
ctagtaagga aaaatccttg ttacagctgt cctataggtt gtggaagatg ggttagacta 900
aaagatggta cagagtgcgg aggaccggag tatgaaacac tgtggtgttt tggctctgac 960
tgtggttcat atgatttaga tgctataaat gaagctaata tgttatgtaa tgaatatggt 1020
attgatacta ttacctgtgg tgcaacaatt gctgcagcta tggaacttta tcaaagagga 1080
tatgtaaaag atgaagaaat agccggagat aacctatctc tcaagtgggg agatacggag 1140
tctatgattg gctggataaa gaaaatggta tatagtgaag gctttggagc aaagatgaca 1200
aatggttcat ataggctttg tgaaggttat ggagtacctg agtattctat gacagttaaa 1260
aaacaagaaa ttccagcata tgatccaagg ggaatacagg gacatggtat tacctatgca 1320
gttaataata gaggaggatg tcatattaag ggatatatga ttaatcctga aatattaggt 1380
tatccggaaa aacttgatag atttgcatta gatggtaaag cagcctatgc caaaaatgatg 1440 catgatttaa ctgctgtaat tgattcttta ggattgtgca tattcactac atttgggctt 1500
ggaatacagg attatgtaga tatgtataat gcagtagtag gagaatctac ttgtgattca 1560
gattcactat tagaggcagg agatagagta tggactcttg aaaaattatt taatcttgca 1620
gctggaatag acagcagcca ggatactcta ccaaagagat tgttagaaga acctattcca 1680
gatggtccat caaagggaca cgttcatagg ctagatgttc ttctgccaga atattactca 1740
gtacgaggat ggagtaaaga gggtatacct acagaagaaa cattaaagaa attaggatta 1800
gatgaatata taggtaagtt ctag 1824

-continued

<210> SEQ ID NO 18
<211> LENGTH: 1956
<212> TYPE: DNA
<213> ORGANISM: Clostriduim ragsdalei

<400> SEQUENCE: 18

```
atggaacaaa attgcaccag aatggaacag tttgcttggt gtaataccct caaaacacaa     60
tattttatta ttggcatggt ttatgctaca tataataatt gtttgaataa tcaatttttt    120
aggagggttt ttatgtacgg atataatggt aaggtattaa gaattaatct aagtagtaaa    180
acttatatag tggaagaatt gaaaattgac aaagctaaaa aatttatagg tgcaagaggt    240
ttaggcgtaa aaaccttatt tgacgaagta gatccaaagg tagatccatt atcacctgat    300
aacaaattta ttatagcagc gggaccactt acaggtgcgc ctgttccaac aagcggaaga    360
ttcatggtag ttactaaatc acctttaaca ggaactattg ctattgcaaa ttcaggtgga    420
aaatggggag cagaattcaa agcagctgga tacgatatga taatcgttga aggtaaatct    480
gataaagaag tttatgtaaa tatagtagat gataaagtag aatttaggga tgcttctcat    540
gtttggggaa aactaacaga agaaactaca aaaatgcttc aacaggaaac agattcgaga    600
gctaaggttt tatgcatagg accagctggg gaaaaattat cacttatggc agcagttatg    660
aatgatgttg atagaacagc aggacgtggt ggtgttggag ctgttatggg ctcaaagaac    720
ttaaaagcta ttgtagttaa aggaagcgga aaagtaaaat tatttgatga gcaaaaagtg    780
aaagaagtag cacttgagaa aacaaatatt ttaagaaaag atccagtagc tggtggagga    840
cttccaacat acggaacagc tgtacttgtt aatattataa atgaaaatgg cgtacatcca    900
gtaaaaaatt tccaaaaatc ttatacagat caggcagata agatcagtgg agaaacttta    960
actaaagatt gcttagttag aaaaaatcct tgctataggt gtccaattgc ctgtggaaga   1020
tgggtaaaac ttgatgatgg aactgaatgt ggaggaccag aatatgaaac attatggtca   1080
tttggatctg attgtgatgt atacgatata aatgctgtaa atacagcaaa tatgttgtgt   1140
aatgaatatg gattagatac cattacagca ggatgtacta ttgcagcagc tatggaactt   1200
tatcaaagag gttatattaa ggatgaagaa atagcagcag atggattgtc acttaattgg   1260
ggagatgcta agtccatggt tgaatgggta aagaaaatgg gacttagaga aggatttgga   1320
gacaagatgg cagatggttc atacagactt tgtgactcat acggtgtacc tgagtattca   1380
atgactgtaa aaaaacaaga aatcccagca tatgacccaa gaggaataca gggacatggt   1440
ataacttatg ctgttaacaa taggggaggg tgtcatatta agggatatat ggtaagccct   1500
gaaatacttg gttatccaga aaaacttgat agacttgcag tggaaggaaa agcaggatat   1560
gctagagtat tccatgattt aacagctgtt atagattcac ttggattatg tattttttaca   1620
acatttggtc ttggtgcaca ggattatgtt gatttgtata atgcagtagt tggtggagaa   1680
ttacatgatg tagactcttt aatgttagct ggagatagaa tatggacttt agaaaaaata   1740
tttaacttaa aggcaggcat agatagttca caggatactc ttccaaagag attgcttgag   1800
gaaccagttc cagaaggacc atcaaaagga gagattcata gattagatgt acttcttcct   1860
gaatattatt cagtacgtgg atgggataaa aatggtatac ctacagagga aacgttaaag   1920
aaattaggat tagatgaata tgtaggtaag ttttaa                             1956
```

<210> SEQ ID NO 19
<211> LENGTH: 1824
<212> TYPE: DNA
<213> ORGANISM: Clostriduim ragsdalei

<400> SEQUENCE: 19

```
atgtacggat atagtggaaa agtattaaga attaatttaa gtaataaaac ttataaagct     60
gaagaattga aaattgatga agctaaaaaa tttataggag ctagggggct aggtgtaaaa    120
actttacttg atgaaataga tcccaaaata gatccattat cacccgataa taaatttatt    180
atcgcaacag gaccacttac aggagcacct gttccaacaa gtggtagatt tatggtaatt    240
actaaagcac ctttaacagg aactattggt attgcaaatt caggcggaaa atggggagct    300
gagttaaaaa cagctggata cgatatggta atcgttgaag gtaaatcaga taaaccagtt    360
tatgtaaata tagtagacga taaagtagaa tttaaggatg cttctcatgt ttggggaaag    420
ttaacagagg aaactacaaa aatgcttcaa aatgaaattg atgcaaaggc taaagtttta    480
tgcataggac cagctggaga aaatttgtca cttatggcag cagttatgaa tgatatcgac    540
agaacagcag gtcgtggtgg tgttggagct gttatgggtt ccaaaaactt aaaagctatc    600
gtagttaaag gaagcggaaa agtaaaatta tttgatgagg aaaaagtaaa agctgtatca    660
cttcagaaat cagatatttt aagaaaagat ccagtagctg gtggaggcct tccaacgtac    720
ggaacagctg tgcttgttaa tataattaac gaaaacggaa taaaccccgt aagaaatttt    780
caggaatctt atacagatga agcagataag gttagtggag aaactatgac tcaggagtgt    840
ttggttagaa aaaatccttg ctatagatgc ccaattgctt gtggaaggtg ggtaagactt    900
gatgatggaa ctgaatgtgg gggaccagaa tatgaaacat tatggtcatt tggatctgat    960
tgtgatgtat atgatttaaa tgctgtaaat aaagctaata tgttatgtaa tgaatatggg   1020
ttagatacaa tttcagcagg agcaactatt gcatcggcta tggagcttta tcaaagaggt   1080
tatattaagg atgaagaaat agctgcagat ggattatcac ttaaatgggg cgatgctaag   1140
tctatggttg aatgggtaaa aaaaatggga cgtagagaag gatttggagg caagatggca   1200
gatggttcat atagactttg tgaatcctat ggtgtgcctc agtattcaat gagtgtaaag   1260
aagcaggaac ttccagcata cgatccaaga ggagctcaag gacatggttt aacctatgcc   1320
gttaacaata gagggggatg tcatattaaa ggatatatga taagtcctga gatacttgga   1380
tatccagaaa agcttgatag attttcaata gaaggaaaac cagcatatgc taaagtattc   1440
catgatttaa cagcagttat agattccctt ggattatgta tctttacaac ttttggtctt   1500
ggtgcccaag attatgttga tatgtacaat gcggtagttg ggggggaatt acatgatgta   1560
gattctttaa tgttagctgg agatagagta tggactttag aaaaaatatt taacttaaaa   1620
gcaggtgtag gtagttcaca agatactctt ccaaagagat tgcttgagga agaagttgta   1680
gaagggccat caaaagggca tgttcataga ttagatgaat tagtacctga gtattactca   1740
gtaagaggat gggataagaa tggtgttcct acagaagaaa ctttaaagaa gcttggatta   1800
gaagagtata ttgggaaaat ttag                                           1824
```

<210> SEQ ID NO 20
<211> LENGTH: 1056
<212> TYPE: DNA
<213> ORGANISM: Clostridium ljungdahlii

<400> SEQUENCE: 20

```
atgaaaggtt ttgcaatgtt aggtattaac aaattaggat ggattgaaaa gaaaaaccca     60
gtgccaggtc cttatgatgc gattgtacat cctctagctg tatccccatg tacatcagat    120
atacatacgg tttttgaagg agcacttggt aatagggaaa atatgatttt aggccatgaa    180
gctgtaggtg aaatagccga agttggcagc gaagttaaag attttaaagt tggcgataga    240
```

-continued

```
gttatcgtac catgcacaac acctgactgg agatctttag aagtccaagc tggttttcag    300

cagcattcaa acggtatgct tgcaggatgg aagttttcca attttaaaga tggtgtattt    360

gcagattact ttcatgtaaa cgatgcagat atgaatcttg ccatactccc agatgaaata    420

cctttagaaa gtgcagttat gatgacagac atgatgacta ctggttttca tggagcagaa    480

cttgcagaca taaaaatggg ctccagcgtt gtagtaattg gtataggagc tgttggatta    540

atgggaatag ccggttccaa acttcgagga gcaggcagaa ttatcggtgt tggaagcaga    600

cctgtttgtg ttgaaacagc taaattttat ggagcaactg atattgtaaa ttataaaaat    660

ggtgatatag ttgaacaaat catggactta actcatggta aaggtgtaga ccgtgtaatc    720

atggcaggcg gtggtgctga aacactagca caagcagtaa ctatggttaa acctggcggc    780

gtaatttcta acatcaacta ccatggaagc ggtgatactt taccaatacc tcgtgttcaa    840

tggggctgcg gcatggctca caaaactata agaggaggat tatgccccgg cggacgtctt    900

agaatggaaa tgctaagaga tcttgttcta tataaacgtg ttgatttgag taaacttgtt    960

actcatgtat ttgatggtgc agaaaatatt gaaaaggccc ttttgcttat gaaaaataag   1020

ccaaaagatt taattaaatc agtagttaca ttctaa                             1056


<210> SEQ ID NO 21
<211> LENGTH: 2613
<212> TYPE: DNA
<213> ORGANISM: Clostridium ljungdahlii

<400> SEQUENCE: 21

atgaaagtta caaacgtaga agaactaatg aaaagactag aagaaataaa ggatgctcaa     60

aagaaatttg ctacatatac tcaagaacaa gtggatgaaa tttttagaca agcagctatg    120

gcagctaata gtgctagaat agaactagct aaaatggcag tagaagaaag cggaatggga    180

attgtagaag acaaggtcat taaaaatcac tttgcctcag aatatatata taacaaatat    240

aaggatgaaa aaacctgtgg agttttagag agagatgcag gatttggtat agttagaatt    300

gcggaacctg taggagttat cgcagcagta gttccaacaa ctaatccaac atctacagca    360

atatttaaat cactaatagc tttaaaaact agaaatggta taattttttc accccatcca    420

agggcaaaga aatcaactat tgcagcagct aaaatagtac ttgacgctgc agttaaagct    480

ggtgctcctg aaggaattat aggatggata gatgaacctt ccattgaact ttcacaggtg    540

gtaatgggag aagcaaattt aattcttgca actggtggcc cgggtatggt taaggctgcc    600

tattcttcag gcaaacctgc tgtgggagtt ggtccaggta acacacctgc tgtaattgat    660

gaaagtgccg acattaaaat ggcagtaaat tcaatattac tatcaaagac ttttgataat    720

ggtatgattt gtgcctcaga gcagtcagta atagttttag actcaatata tgaggaagtt    780

aaaaaagaat ttgcttatag ggtgcttat atattaagta aggatgaaac agataaggtt    840

ggaaaaataa ttttaaaaaa tggagcctta aatgcaggta ttgtaggaca acctgctttt    900

aaaatagcac agctggcagg agtggatgta ccagaaaaag ctaaagtact tataggagag    960

gtagaatcgg tagaacttga agaaccattt tctcatgaaa agttatctcc agttttagct   1020

atgtacaggg caagaaattt tgaggatgcc attgcaaaaa ctgataaact ggttaggtca   1080

ggtggatttg gacatacatc ttcattatat gtaaatccaa tgacagagaa agcaaaagta   1140

gaaaaattta gtactatgat gaaaacatca agaactataa ttaacacacc ttcatcccaa   1200

ggtggtatag gtgatatata taactttaaa ctagctcctt ctttgacatt aggctgcggt   1260

tcctggggag gaaattctgt atccgaaaat gttgggccta aacatttatt aaacataaaa   1320
```

agtgttgctg agaggagaga aaatatgctt tggtttagag tacctgaaaa ggtttatttc 1380
aaatatggta gtcttggagt tgcattaaaa gaattaaaag ttatgaataa gaagaaagta 1440
tttatagtaa cagataaagt tctttatcaa ttaggttatg tggacaaagt tacaaaagtt 1500
cttgaggaac taaaaatttc ctataaggta tttacagatg tagaaccaga tccaacccct 1560
gctacagcta aaaaaggtgc agcagaactg ctttcctatg aaccggatac aattatatca 1620
gttggtggtg gctcagcaat ggatgcagct aagatcatgt gggtaatgta tgagcatcca 1680
gaagtaaaat ttgaagattt agctatgaga tttatggata taagaaagag agtatatgtt 1740
ttccctaaga tgggagaaaa ggcaatgatg atttcagtag caacatccgc aggaacaggg 1800
tcggaagtta ctccatttgc agtaatcact gatgaaaaaa caggagctaa atatccatta 1860
gctgattatg aactaactcc agacatggct atagttgatg cagaacttat gatgggaatg 1920
ccaagaggac ttacagcagc ttcgggtata gatgcattaa cccatgcact ggaggcatat 1980
gtgtcaataa tggctacaga atttaccaat ggattagccc ttgaagcagt aaagttgata 2040
tttgaatatt taccaaaagc ttatacagaa ggtacaacta atgtaaaggc aagagaaaag 2100
atggttcatg cttcatgtat tgcaggtatg gcctttgcaa atgcattttt aggggtatgc 2160
cactctatgg cacataaatt gggagcacag catcacatac cacatggaat tgccaatgca 2220
cttatgatag atgaagttat aaaattcaat gctgtagatg atccaataaa acaagctgca 2280
tttccccaat acgagtatcc aaatgctagg tatagatatg ctcagatagc tgattgtctg 2340
aacttgggag gaaatacaga agaggaaaag gtacaactat taataaatgc tatagatgat 2400
ttaaaagcta agttaaatat tccagaaact ataaaagaag caggagtttc agaagataaa 2460
ttctatgcta ctttagataa aatgtcagaa ttagcttttg atgatcagtg tacaggagct 2520
aatccaagat atccactgat aagtgaaata aaacaaatgt atataaatgt ttttgataaa 2580
accgaaccaa ttgtagaaga tgaagaaaag taa 2613

<210> SEQ ID NO 22
<211> LENGTH: 2688
<212> TYPE: DNA
<213> ORGANISM: Clostridium ljungdahlii

<400> SEQUENCE: 22
atgagaaatt tgtttatatt taacagcata aaaaataaga aagaggtgtc attaatgaag 60
gtaactaagg taactaacgt tgaagaatta atgaaaaagt tagatgaagt aacggctgct 120
caaaagaaat tttctagcta tactcaagaa caagtggatg aaattttcag gcaggcagct 180
atggcagcca atagtgctag aatagactta gctaaaatgg cagtggaaga aagcggaatg 240
ggaattgtag aagacaaggt cattaaaaat cattttgttg cagagtatat atataacaaa 300
tataagggtg aaaaaacctg tggagttctg gaacaagatg aaggctttgg tatggttaga 360
attgcagaac ctgtaggagt tattgcagca gtagtcccaa caactaatcc aacatctaca 420
gcaatattta aatcactaat agctttaaaa actagaaatg gtatagtttt ttcgccacat 480
ccaagggcaa aaaaatcaac tattgcagca gctaagatag tacttgatgc tgcagttaaa 540
gctggtgctc ctgaaggaat tataggatgg atagatgaac cttctattga actttcacag 600
gtggtaatga aagaagcaga tctaattctt gcaactggtg gaccaggtat ggttaaggct 660
gcctattctt caggaaagcc tgctatagga gttggtccag gtaacacgcc tgctgtaatt 720
gatgaaagtg ctgacattaa aatggcagta aattcaatac tattatcaaa aacttttgat 780
aatggtatga tttgtgcttc agagcagtca gtagtagttg caagctcaat atacgatgaa 840

-continued gtcaagaaag agtttgcaga tagaggagca tatatattaa gtaaggatga aacagagaag 900
gttggaaaaa caattataat taatggagcc ttaaatgctg gcattgtagg gcaaagtgct 960
tttaaaatag cacagatggc aggagtgagt gtaccagaag atgctaaagt acttatagga 1020
gaagttaaat cagtagaacc ggaagaagag ccctttgcgc atgaaaagct atctccagtt 1080
ttagctatgt acaaagcaaa agattttgac gaagcactcc taaaggctgg aagattagtt 1140
gaacgaggtg gaattgggca tacatctgta ttatatgtaa atgcaatgac ggaaaaagta 1200
aaggtagaaa agttcagaga aactatgaag actggtagaa cattgataaa tatgccttca 1260
gcacaaggtg ctataggaga tatatataac tttaagctag ctccttcttt gacactaggt 1320
tgtggttcct ggggaggaaa ctctgtatca gaaaatgttg gtcctaaaca tttattaaac 1380
ataaagagtg ttgctgagag gagagaaaat atgctttggt ttagagtacc tgaaaaggtt 1440
tatttcaaat atggtagtct tggagttgca ctaaaagaac tgagaattat ggagaagaaa 1500
aaggcattta tagtaacgga taaagttctt tatcaattag gttatgtaga taaaattaca 1560
aaaaatctgg atgaattaag agtttcatat aaaatattta cagatgtaga accagatcca 1620
acccttgcta cagctaaaaa aggtgcagca gaactgttag cttatgaacc agatacaatt 1680
atagcagtcg gtggtggttc agcaatggat gcagccaaga tcatgtgggt aatgtatgag 1740
catccagaag taagatttga agatttagct atgagattta tggatataag aaagagagtg 1800
tatgttttcc ctaaaatggg agaaaaggca atgatgattt cagtagcaac atccgcagga 1860
acagggtcgg aagttacgcc atttgcagta attacggatg aaagaacagg agctaaatat 1920
cctctggctg attatgaatt gactccaaac atggctatag ttgatgcaga acttatgatg 1980
ggaatgccaa agggactaac agcagcttca ggtatagatg cattaaccca tgcgctggag 2040
gcctatgtat caataatggc ttcagaatat accaatggat tggctcttga agcaacaaga 2100
ttagtattta aatatttgcc aatagcttat acagaaggta caactaatgt aaaggcaaga 2160
gaaaaaatgg ctcatgcttc atgtattgca ggtatggcct ttgccaatgc atttttaggg 2220
gtatgccact ccatggcaca taaattggga gcacagcacc acataccaca tggaattgcc 2280
aatgcactta tgatagatga agttataaag ttcaatgctg tagaggctcc aaggaaacaa 2340
gcggcatttc cacaatataa atatccaaat gttaaaagaa gatatgctag aatagctgat 2400
tacttaaatt taggtggaag tacagatgat gaaaaagtac aatttttaat aaatgctata 2460
gatgacttga aaaccaagtt aaatattcca aagactatta aagaagcggg agtttcagaa 2520
gataaattct atgctacttt agatacaatg tcagaactgg cttttgatga tcaatgtaca 2580
ggagctaatc caagatatcc attaatagga gaaataaaac aaatgtatat aaatgcattt 2640
gatacaccaa aggcaactgt ggagaagaaa acaagaaaga aaaaataa 2688

<210> SEQ ID NO 23
<211> LENGTH: 1143
<212> TYPE: DNA
<213> ORGANISM: Clostridium ljungdahlii

<400> SEQUENCE: 23
atgactatat ttaacattaa acccataatt tgttttaata gagggtcaat agagtatttg 60
aaaaacataa agaataaaag agtgtgtata gttacggacc cgtttatgct taaatcaggt 120
actgcagata aaataattga catattaaaa gataataaag ttgagtatga aattttttca 180
gagataaaac ctgatccacc gattgaaatc gttgctatgg gagtaaataa aatgagaata 240
tttaaaccag atgtagtaat tgcattaggc ggcggttcat caattgatgc tacgaaaagc 300
attatattct ttactattaa aatattaaat actaatggag gcaattataa aaaaccatta 360
tttgtagcta ttccaactac tagtggtaca ggatcagaag ttacttcttt ttcagtaatt 420
acaatgggag gtacaaaatt tcctttgatt aatgatgaat tagttccaga tatagctata 480
attgatgcaa atcttgttaa aacagtgcct caacgaataa cagcagatac tggaatggat 540
gttttgactc atgccattga ggcgtatgtt tcgacaaaaa gctctgatta tacagatgcg 600
ctggctgaaa aggttgtaaa attagtattt gactatttac taagggctta tagagatgga 660
aacgatgtgc ttgcaagaga aaaattacat aatgcatctt gcatggctgg tatggcattt 720
acaaatgcat ctttaggaat taatcacagt atggcacata cattaggggg gaaatttcat 780
ataccacatg gtagggcaaa tgcaatttta ttaccgtatg tcattgagta taatgctaat 840
ttaaaatcag aaaatgaaac agaatcagga aaaaagtatg ctaatttgtc tagaatctta 900
gggttacctt gtgcttctac aaatgaggga gtaagaagta ttattgctgc aataaaaata 960
ttaatgaatg caactaatac acctatgaac ttacaggaag taaacataga taaacttgat 1020
tttttaaacg aactagagaa tatggtaaat gatgctttaa atgataaatg cacagctact 1080
aatccaagga aaactagcaa agaagaaata gctaaattgt ttgaagaagt ttatggtaaa 1140
tag 1143

<210> SEQ ID NO 24
<211> LENGTH: 1149
<212> TYPE: DNA
<213> ORGANISM: Clostridium ljungdahlii

<400> SEQUENCE: 24
atggaagaca agtttgaaaa ttttaatttg aaatccaaga tttattttaa tagggaatct 60
attcaacttt tagagcaagt cactggttct cgagcattta ttgttgcaga tgctattatg 120
ggaaaacttg gatatcttca aaaagtaata gattacctaa gcaaagctgg aataagttcc 180
gttgttttta cgggggtaca ccctgatcca gacgtcaatg taattgcaga tgcaatgaaa 240
ttgtacaaaa aaagcgacgc agatgttctc gtagcactag gtggaggatc cagtattgat 300
accgctaagg gaataatgta ttttgcatgt aatttaggaa aagcaatggg ccaagaaatg 360
aaaaaacctc tatttattgc aattccatca acaagtggta caggctctga agtaacaaac 420
tttactgtta ttacttctca gaaagaaaag gtatgcatta tagatgattt tattgcacca 480
gatgttgcaa tacttgactc aagttgtatt gatggtctgc ctcagcgtat tgtagcagat 540
actggtatag atgttctagt tcattctatt gaagcctatg tttccaaaaa agcaactgac 600
tttacagacg ctcttgctga aaaagcagtt aaattaattt ttgagaatct tccaaaaatt 660
tataacgata gtaaggattc cgaagctcga gatcatgttc aaaacgcttc ctgtatagca 720
ggaatagcat ttacaaatgc tggtcttgga attaatcaca gcttggctca tgctatgggt 780
ggatctttcc acattcctca cggccgatcc aatgcacttc tacttaatgc agtaatggaa 840
tacaacgcta gcttggttgg aaatgcaagc gaacatgcta tggaaaaata cgcaaaacta 900
gcatcaattc tacaccttcc agctcgaaca actcgcgaag gcgctgtaag ttttattgaa 960
gctgtagata aattaataaa atccctaggt gttgaagata atattcgatc tcttgggatt 1020
aaagaagatg agtttcaaag tgctctaaat catatggcag aaacagcaat gcaagataga 1080
tgcactccaa ctaatcctag aaaaccttct aaagaagaac ttatacatat ttatcaaaaa 1140
tgttattaa 1149

<210> SEQ ID NO 25
<211> LENGTH: 918
<212> TYPE: DNA
<213> ORGANISM: Clostridium ljungdahlii

<400> SEQUENCE: 25
atgctaggag gaatagattt gattttttac tatccttact ttggttacaa agtaaagtgt 60
aaaagggttc cagtagcttt tccacctcaa caccaagctg tacagcccgg attagagaca 120
cttatgaacc ccaagcctat atttgataat ccagactatg ctgggagtga taaattaaaa 180
aataaggtcg ccctaattac tggaggagat agtggtattg gcagagctgt atctctagct 240
tttgccaaag aaggtgcaga cattagtatt gtgtacttca atgaacatgt ggatgcagct 300
aaaacaaagg ctttagtaga atctcaagga agaaagtgcc tcttaatttc tggagattta 360
agagaagagt ccttttgtaa aaaaatagtc aaagatacac ttgatgcctt tggtcaccta 420
gatatactag ttaataatgc aggtgttcaa tttcctcaaa acagtcttga aaatatctct 480
acagaacaat tggaagatac ttttaggaca aatatttttc ccttattcca cgttactaaa 540
gctgccctac ctcacttaaa aaaagaaagc agcattatta ataccgcttc aattacagct 600
tacatgggta ataagctact tattgattat tcttctacaa aaggagccat tgtgagcttt 660
acccgttcat tagctctttc tcttgtatca aaagggataa gagtcaatgg aattgctcct 720
ggacctgttt ggacacctct tataccatca agttattcag caaagtatgt ggaaactttt 780
ggcttagata ctcctatgaa aagagctggt caacctgtgg aattggcacc tgcttatgtt 840
tacttagcat ctgacgattc tacttttgtt actggtcaaa ttctacatgt aaatggtgga 900
ggctttatag gatcataa 918

<210> SEQ ID NO 26
<211> LENGTH: 867
<212> TYPE: DNA
<213> ORGANISM: Clostridium ljungdahlii

<400> SEQUENCE: 26
atgaattttc caacatcttt tccaaagcag catcagaatc atcatccggg atttcagtat 60
gaaatgaatc ctatgcctat atgtgatgat gctgtgtata atagaaaagg agaactttta 120
aaaggaaaaa ctgccataat tacaggtggt gacagcggta taggtagagc tgtttctata 180
gcttatgcga accaaggtgc agatgtagta attgtatact taaatgaaca aaaagatgct 240
gaggaagcta aaagacttgt ggaaaccaag ggaacaaagt gcacacttat agcaggtgat 300
attagtgatg taaatttttg caatagcgtt gtagaaaaaa ccataagtga atatgggaaa 360
atagatatac tagttaataa tgctgctgtc caatatgaat gtactgatat aaagcagtta 420
tcagatgaac aatttgacag aacttttaaa accaatgcat atgggacttt ctatatgaca 480
agggcagcaa tgaattattt aaaatcagga gcatgtataa taaatacagc ttctatagtg 540
gcttttaaag gaagtgccac acttatagat tattctatga caaaaggtgc aatagtagct 600
tttactagat cattatctac tgcacttgca aaggggaaga ctggaataag ggtaaatgca 660
gttgcaccag ggccaatctg gacaccactt ataccatctt gttttgatga aacaaagact 720
tcccagtttg gtgaggatat gccaatggca agagccggtc agcctgtgga atgtgcagga 780
gcttatgtat ttttggcttc tgaaaatgca tcttatatta caggtcagac tatccatgta 840
aatggaggag aaatagtgaa cggttga 867

<210> SEQ ID NO 27
<211> LENGTH: 789

<212> TYPE: DNA
<213> ORGANISM: Clostridium ljungdahlii

<400> SEQUENCE: 27
atgactttaa ataatgaaaa gactgtttta attacaggag cttcaagtgg aataggactt 60
gaacttgcaa aattattttc taaggatgga tataatttaa tacttgtagc tagaagtgaa 120
aacaaattag aagaaatagc aaaaaattta ataaaaaaat ataatattaa tgtacatata 180
ataaaagaag atctttcaaa aagagaatct gtaaaagatc tatttttaaa agtgcagcag 240
ctaggcataa gggtaactac tcttgttaat aatgcaggtg caggttactg tggacttttt 300
catgaaattg atatagacaa agatgaaaaa atgataggtt taaacattga agctattact 360
tatttaacga agttattttc aaaagaaatg ataaagttaa aaaaagggag tatattaaat 420
gtggcatcta cgggttctta tgaaccagga ccttatattg cagtatacta tgcgtctaaa 480
gcatatgtgc tatccttttc tcaagccctt gaaaatgagc taaaaccata tggtataaaa 540
gtatgtactc tgtgcccagg agctactaaa actggatttt ctaaaaatgc aggtaaaaaa 600
gatataaaaa ctgctatgag tgctgaaaaa actgctgaga tagcttatag aggatttatg 660
aaaaataaat ctgttataat accaggattt tttaataaaa tagctgtttt attttgtaag 720
ctattgccag gtaagatttc tgcggttgtt gttagaagaa tacaggaaaa tgtaactaaa 780
aatttttaa 789

<210> SEQ ID NO 28
<211> LENGTH: 846
<212> TYPE: DNA
<213> ORGANISM: Clostridium ljungdahlii

<400> SEQUENCE: 28
atgatttatt atgtacctaa gttttattac tggaggttaa ttgttatgaa aaatgaaata 60
gttgttttaa ttactggatg ctctacagga attgggagag agctttgtaa tatattatct 120
cataaaggat gtacggttgt tgcaacagca agaaatgtgg aagccttaaa ggatttatct 180
gcattcttaa aattaccgct agatgttacc aaaaaagaat ctattcacag cacaataaat 240
caagttatat caaaatttca taaaattgat attcttataa ataacgcagg ttattcactt 300
agaggagctt tagaagaaat tgatgtaaat agttctaaaa gtatgtttga tgtaaatgta 360
tttggtataa ttaacatggt tcaggaggtt attccagaaa tgcgtaaaaa gcaatctggt 420
aagattataa atattggttc catttcagga aaatttgttc aatccatcaa tggggtttat 480
tgtgcatcaa aatttgcagt tgaggcatta agtgacacac tgcgtttaga attacacagc 540
tataatattc agaccactgt cattgagcca ggtcccatga aaacccattt ttttaataca 600
ttagtggata attcagggga tcttatggga aattcccaat cttgttattc acatttttat 660
aaatcagatg ataaatatag aaaaaagcaa aaacaagctg atcctaaaga agcagcacaa 720
gctattagta atataatttt gaaaaaacga attaatgctc gttataaagt tactgttccc 780
ttcatatata gtatggttac atattttcct gatttcctaa gagaatattt tatgaaaaag 840
agataa 846

<210> SEQ ID NO 29
<211> LENGTH: 1824
<212> TYPE: DNA
<213> ORGANISM: Clostridium ljungdahlii

<400> SEQUENCE: 29
atgtatggtt atgatggtaa agtattaaga attaatttaa aagaaagaac ttgcaaatca 60

```
gaaaatttag atttagataa agctaaaaag tttataggtt gtaggggact aggtgttaaa    120

actttatttg atgaaataga tcctaaaata gatgcattat caccagaaaa taaatttata    180

attgtaacag gtcctttaac tggagctccg gttccaacta gtggaaggtt tatggtagtt    240

actaaagcac cgcttacagg aactatagga atttcaaatt cgggtggaaa atggggagta    300

gacttaaaaa aagctggttg ggatatgata atagtagagg ataaggctga ttcaccagtt    360

tacattgaaa tagtagatga taaggtagaa attaaagacg cgtcacagct ttggggaaaa    420

gttacatcag aaactacaaa agagttagaa aagataactg agaataaatc aaaggtatta    480

tgtataggac ctgctggtga acgattgtct cttatggcag cagttatgaa tgatgtagat    540

agaactgcag caagaggcgg cgttggtgca gttatgggat ctaaaaactt aaaagctatt    600

acagttaaag gaactggaaa aatagcttta gctgataaag aaaaagtaaa aaaagtgtcc    660

gtagaaaaaa ttacaacatt aaaaaatgat ccagtagctg gtcagggaat gccaacttat    720

ggtacagcta tactggttaa tataataaat gaaaatggag ttcatcctgt aaagaatttt    780

caagagtctt atacgaatca agcagataaa ataagtggag agactcttac tgctaaccaa    840

ctagtaagga aaaatccttg ttacagctgt cctataggtt gtggaagatg ggttagacta    900

aaagatggca cagagtgcgg aggaccagaa tatgaaacac tgtggtgttt tggatctgac    960

tgtggttcat atgatttaga tgctataaat gaagctaata tgttatgtaa tgaatatggt   1020

attgatacta ttacttgtgg tgcaacaatt gctgcagcta tggaacttta tcaaagagga   1080

tatataaaag acgaagaaat agctggagat aacctatctc tcaagtgggg tgatacggaa   1140

tctatgattg gctggataaa gagaatggta tatagtgaag gctttggagc aaagatgaca   1200

aatggttcat ataggctttg tgaaggttat ggagcaccgg agtattctat gacagttaaa   1260

aagcaggaaa ttccagcata tgatccaagg ggaatacagg gacacggtat tacctatgca   1320

gttaataata gaggaggctg tcatattaag ggatatatga ttaaccctga aatattaggt   1380

tatcctgaaa aacttgatag atttgcatta gatggtaaag cagcttatgc caaattattt   1440

catgatttaa ctgctgtaat tgattcttta ggattgtgca tattcactac atttgggctt   1500

ggaatacagg attatgtaga tatgtataat gcagtagtag gagaatctac ttatgatgca   1560

gattcactat tagaggcagg agatagaatc tggactcttg agaaattatt taatcttgca   1620

gctggaatag acagcagcca ggatactcta ccaaagagat tgttagaaga acctattcca   1680

gatggcccat caaagggaga agttcatagg ctagatgttc ttctgccaga atattactca   1740

gtacgaggat ggagtaaaga gggtatacct acagaagaaa cattaaagaa attaggatta   1800

gatgaatata taggtaagtt ctag                                          1824
```

<210> SEQ ID NO 30
<211> LENGTH: 1826
<212> TYPE: DNA
<213> ORGANISM: Clostridium ljungdahlii

<400> SEQUENCE: 30

```
aratgtacgg atataagggt aaggtattaa gaattaatct aagtagtaaa acttatatag     60

tggaagaatt gaaaattgac aaagctaaaa aatttatagg tgcaagaggg ttaggcgtaa    120

aaaccttatt tgacgaagta gatccaaagg tagatccatt atcacctgat aacaaattta    180

ttatagcagc gggaccactt acaggtgcac ctgttccaac aagcggaaga ttcatggtag    240

ttactaaatc acctttaaca ggaactattg ctattgcaaa ttcaggtgga aaatggggag    300

cagaattcaa agcagctgga tacgatatga taatcgttga aggtaaatct gataaagaag    360
```

-continued

```
tttatgtaaa tatagtagat gataaagtag aatttaggga tgcttctcat gtttggggaa    420
aactaacaga agaaactaca aaaatgcttc aacaggaaac agattcgaga gctaaggttt    480
tatgcatagg accagctggg gaaaagttat cacttatggc agcagttatg aatgatgttg    540
atagaacagc aggacgtggt ggtgttggag ctgttatggg ttcaaagaac ttaaaagcta    600
ttgtagttaa aggaagcgga aaagtaaaat tatttgatga acaaaaagtg aaggaagtag    660
cacttgagaa aacaaatatt ttaagaaaag atccagtagc tggtggagga cttccaacat    720
acggaacagc tgtacttgtt aatattataa atgaaaatgg tgtacatcca gtaaagaatt    780
ttcaaaaatc ttatacagat caagcagata agatcagtgg agaaacttta actaaagatt    840
gcttagttag aaaaaatcct tgctataggt gtccaattgc ctgtggaaga tgggtaaaac    900
ttgatgatgg aactgaatgt ggaggaccag aatatgaaac attatggtca tttggatctg    960
attgtgatgt atacgatata aatgctgtaa atacagcaaa tatgttgtgt aatgaatatg   1020
gattagatac cattacagca ggatgtacta ttgcagcagc tatggaactt tatcaaagag   1080
gttatattaa ggatgaagaa atagcagcag atggattgtc acttaattgg ggagatgcta   1140
agtccatggt tgaatgggta aagaaaatgg gacttagaga aggatttgga gacaagatgg   1200
cagatggttc atacagactt tgtgactcat acggtgtacc tgagtattca atgactgtaa   1260
aaaaacagga acttccagca tatgacccaa gaggaataca gggacatggt attacttatg   1320
ctgttaacaa taggggagga tgtcacatta agggatatat ggtaagtcct gaaatacttg   1380
gctatccaga aaaacttgat agacttgcag tggaaggaaa agcaggatat gctagagtat   1440
tccatgattt aacagctgtt atagattcac ttggattatg tatttttaca acatttggtc   1500
ttggtgcaca ggattatgtt gatatgtata atgcagtagt tggtggagaa ttacatgatg   1560
taaattcttt aatgttagct ggagatagaa tatggacttt agaaaaaata tttaacttaa   1620
aggcaggcat agatagttca caggatactc ttccaaagag attgcttgaa gaacaaattc   1680
cagaaggacc atcaaaagga gaagttcata agttagatgt actactacct gaatattatt   1740
cagtacgtgg atgggataaa aatggtattc ctacagagga aacgttaaag aaattaggat   1800
tagatgaata cgtaggtaag ctttag                                        1826
```

<210> SEQ ID NO 31
<211> LENGTH: 915
<212> TYPE: DNA
<213> ORGANISM: Clostriduim carboxidivorans

<400> SEQUENCE: 31

```
atgattaaaa atttacaaga agttttagaa aaggctaaaa atcaagaaac aaagaagata     60
gcagtagcgg tagctcaaga tagaccagta cttgaagcta ttagggatgc taaagaacaa    120
ggaatatcgg aagcaatatt agttggtgac aaagcaaaga tggaagctat agcagcagaa    180
atagaaatgg atttaacaaa atttgaaatt gttaatgaag aaaatcctgt taaagctgca    240
ttaaaggctg tagaattagt ttcttcaggt aaagctgata tgttaatgaa aggtcttatt    300
gatacagcta actttttaag agcagtttta aacaaagaag ttggtttaag aacaggaaaa    360
ttaatgtctc atgtagcagt tttgaaata cctaagattg atagattaat atttttaaca    420
gatgcagctt ttaatatgta tccagaactt aaagataaaa tagatatagt taaaaatgct    480
gtaacagttg cgcatgcagt aggaatagaa acaccaaaag tagcaccagt atgtgctgta    540
gaagtagtaa atcctagtat gcaggcaact atagatgcat caataatttc aaaaatgaat    600
gacagaggac aaataaaagg atgcttaatt gatggaccat tagcattaga taatgcatta    660
```

-continued

```
tctgtagaag ctgctgcaca taagggagta aaaggagaag tagcaggaag agcagatata    720

ttattaatgc caaatataga agcaggaaat ataatgtaca aaactttagc ttatacaaca    780

gaatctaaga gtggagcttt actagtagga acatcagcac cagtagtatt gacatcaaga    840

aacgatagtc atgaaacaaa aatgaatgca atagcattag cagcgttagt tgcacatcaa    900

ttaaagagaa aataa                                                      915
```

```
<210> SEQ ID NO 32
<211> LENGTH: 1071
<212> TYPE: DNA
<213> ORGANISM: Clostriduim carboxidivorans

<400> SEQUENCE: 32

atgtcatata aattattaat attaaatcca ggatctacat ctaccaaaat aggagtatat     60

gatggagaaa atgaaatttt agaagaaact ttaagacatt cttcagaaga aattgagaaa    120

tatgctacta tttatgatca atttgaattt agaaaagaag ttatattgaa ggttttaaaa    180

gaaaagaatt ttgatattaa tacattagac ggagtagtag gcagaggtgg attattaaaa    240

ccaattgaaa gtggaactta taaagtcaat gatgctatgt tagaagacct aaaagttgga    300

gtgcaaggac agcatgcttc aaatttaggt ggaataatag ctaatgaaat aggaaaatct    360

ataaataaac cagcatttat agtagaccca gttgttgttg atgaattaga tgaagcagct    420

agaatatccg gaatgcctga aatagaaaga ataagtatat tccatgcttt aaatcaaaaa    480

gcagtagcaa agagatatgc aaaagaaaac aataagaagt atgatgaatt aaatttagta    540

gtgacacaca tgggtggcgg agtaactgtt ggagctcaca aaaaaggaag agttgtagat    600

gtagccaatg gtttagatgg agatggacca ttttcaccag aaagaacagg aggacttcct    660

gtaggaggtt taataaagct ttgctatagt ggaaaatata ctttagaaga aatgaagaaa    720

aagataagtg gaaaaggtgg aattgtagct tatctaaata caaatgattt tagggaagta    780

gaacaaaaag cagaaagtgg agataaaaag gcaaagttag tatttgatgc tttcatatta    840

caagtaggta aagaaattgg taaatgtgct gcagttttac atggaaaagt agatgcttta    900

attttaactg gaggaatagc ttatagtaaa actgttacag ctgcaataaa agacatggta    960

gaatttattg caccagttgt agtttatcca ggagaagatg aattattagc attagcacaa   1020

ggcggactta gagtactagg tggagaagaa caagcaaaag aatataagta a            1071
```

```
<210> SEQ ID NO 33
<211> LENGTH: 351
<212> TYPE: PRT
<213> ORGANISM: Clostriduim ragsdalei

<400> SEQUENCE: 33

Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
            20                  25                  30

Ala Val Ser Pro Cys Thr Ser Asp Ile His Thr Val Phe Glu Gly Ala
        35                  40                  45

Leu Gly Asn Arg Glu Asn Met Ile Leu Gly His Glu Ala Val Gly Glu
    50                  55                  60

Ile Ala Glu Val Gly Ser Glu Val Lys Asp Phe Lys Val Gly Asp Arg
65                  70                  75                  80

Val Ile Val Pro Cys Thr Thr Pro Asp Trp Arg Ser Leu Glu Val Gln
                85                  90                  95
```

Ala Gly Phe Gln Gln His Ser Asn Gly Met Leu Ala Gly Trp Lys Phe
100 105 110

Ser Asn Phe Lys Asp Gly Val Phe Ala Asp Tyr Phe His Val Asn Asp
115 120 125

Ala Asp Met Asn Leu Ala Ile Leu Pro Asp Glu Ile Pro Leu Glu Ser
130 135 140

Ala Val Met Met Thr Asp Met Met Thr Thr Gly Phe His Gly Ala Glu
145 150 155 160

Leu Ala Asp Ile Lys Met Gly Ser Ser Val Val Val Ile Gly Ile Gly
165 170 175

Ala Val Gly Leu Met Gly Ile Ala Gly Ser Lys Leu Arg Gly Ala Gly
180 185 190

Arg Ile Ile Gly Val Gly Ser Arg Pro Val Cys Val Glu Thr Ala Lys
195 200 205

Phe Tyr Gly Ala Thr Asp Ile Val Asn Tyr Lys Asn Gly Asp Ile Val
210 215 220

Glu Gln Ile Met Asp Leu Thr His Gly Lys Gly Val Asp Arg Val Ile
225 230 235 240

Met Ala Gly Gly Gly Ala Glu Thr Leu Ala Gln Ala Val Thr Met Val
245 250 255

Lys Pro Gly Gly Val Ile Ser Asn Ile Asn Tyr His Gly Ser Gly Asp
260 265 270

Thr Leu Pro Ile Pro Arg Val Gln Trp Gly Cys Gly Met Ala His Lys
275 280 285

Thr Ile Arg Gly Gly Leu Cys Pro Gly Gly Arg Leu Arg Met Glu Met
290 295 300

Leu Arg Asp Leu Val Leu Tyr Lys Arg Val Asp Leu Ser Lys Leu Val
305 310 315 320

Thr His Val Phe Asp Gly Ala Glu Asn Ile Glu Lys Ala Leu Leu Leu
325 330 335

Met Lys Asn Lys Pro Lys Asp Leu Ile Lys Ser Val Val Thr Phe
340 345 350

<210> SEQ ID NO 34
<211> LENGTH: 351
<212> TYPE: PRT
<213> ORGANISM: Clostridium ljungdahlii

<400> SEQUENCE: 34

Met Lys Gly Phe Ala Met Leu Gly Ile Asn Lys Leu Gly Trp Ile Glu
1 5 10 15

Lys Lys Asn Pro Val Pro Gly Pro Tyr Asp Ala Ile Val His Pro Leu
20 25 30

Ala Val Ser Pro Cys Thr Ser Asp Ile His Thr Val Phe Glu Gly Ala
35 40 45

Leu Gly Asn Arg Glu Asn Met Ile Leu Gly His Glu Ala Val Gly Glu
50 55 60

Ile Ala Glu Val Gly Ser Glu Val Lys Asp Phe Lys Val Gly Asp Arg
65 70 75 80

Val Ile Val Pro Cys Thr Thr Pro Asp Trp Arg Ser Leu Glu Val Gln
85 90 95

Ala Gly Phe Gln Gln His Ser Asn Gly Met Leu Ala Gly Trp Lys Phe
100 105 110

Ser Asn Phe Lys Asp Gly Val Phe Ala Asp Tyr Phe His Val Asn Asp
115 120 125

```
Ala Asp Met Asn Leu Ala Ile Leu Pro Asp Glu Ile Pro Leu Glu Ser
    130                 135                 140

Ala Val Met Met Thr Asp Met Met Thr Thr Gly Phe His Gly Ala Glu
145                 150                 155                 160

Leu Ala Asp Ile Lys Met Gly Ser Ser Val Val Val Ile Gly Ile Gly
                165                 170                 175

Ala Val Gly Leu Met Gly Ile Ala Gly Ser Lys Leu Arg Gly Ala Gly
            180                 185                 190

Arg Ile Ile Gly Val Gly Ser Arg Pro Val Cys Val Glu Thr Ala Lys
        195                 200                 205

Phe Tyr Gly Ala Thr Asp Ile Val Asn Tyr Lys Asn Gly Asp Ile Val
    210                 215                 220

Glu Gln Ile Met Asp Leu Thr His Gly Lys Gly Val Asp Arg Val Ile
225                 230                 235                 240

Met Ala Gly Gly Gly Ala Glu Thr Leu Ala Gln Ala Val Thr Met Val
                245                 250                 255

Lys Pro Gly Gly Val Ile Ser Asn Ile Asn Tyr His Gly Ser Gly Asp
            260                 265                 270

Thr Leu Pro Ile Pro Arg Val Gln Trp Gly Cys Gly Met Ala His Lys
        275                 280                 285

Thr Ile Arg Gly Gly Leu Cys Pro Gly Gly Arg Leu Arg Met Glu Met
    290                 295                 300

Leu Arg Asp Leu Val Leu Tyr Lys Arg Val Asp Leu Ser Lys Leu Val
305                 310                 315                 320

Thr His Val Phe Asp Gly Ala Glu Asn Ile Glu Lys Ala Leu Leu Leu
                325                 330                 335

Met Lys Asn Lys Pro Lys Asp Leu Ile Lys Ser Val Val Thr Phe
            340                 345                 350


<210> SEQ ID NO 35
<211> LENGTH: 352
<212> TYPE: PRT
<213> ORGANISM: Thermoanaerobacter ethanolicus

<400> SEQUENCE: 35

Met Lys Gly Phe Ala Met Leu Ser Ile Gly Lys Val Gly Trp Ile Glu
1               5                   10                  15

Lys Glu Lys Pro Ala Pro Gly Pro Phe Asp Ala Ile Val Arg Pro Leu
            20                  25                  30

Ala Val Ala Pro Cys Thr Ser Asp Ile His Thr Val Phe Glu Gly Ala
        35                  40                  45

Ile Gly Glu Arg His Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Val Val Pro Ala Ile Thr Pro Asp Trp Trp Thr Ser Glu Val Gln
                85                  90                  95

Arg Gly Tyr His Gln His Ser Gly Gly Met Leu Ala Gly Trp Lys Phe
            100                 105                 110

Ser Asn Val Lys Asp Gly Val Phe Gly Glu Phe Phe His Val Asn Asp
        115                 120                 125

Ala Asp Met Asn Leu Ala His Leu Pro Lys Glu Ile Pro Leu Glu Ala
    130                 135                 140

Ala Val Met Ile Pro Asp Met Met Thr Thr Gly Phe His Gly Ala Glu
145                 150                 155                 160
```

-continued

```
Leu Ala Asp Ile Glu Leu Gly Ala Thr Val Ala Val Leu Gly Ile Gly
                165                 170                 175

Pro Val Gly Leu Met Ala Val Ala Gly Ala Lys Leu Arg Gly Ala Gly
            180                 185                 190

Arg Ile Ile Ala Val Gly Ser Arg Pro Val Cys Val Asp Ala Ala Lys
        195                 200                 205

Tyr Tyr Gly Ala Thr Asp Ile Val Asn Tyr Lys Asp Gly Pro Ile Glu
    210                 215                 220

Ser Gln Ile Met Asn Leu Thr Glu Gly Lys Gly Val Asp Ala Ala Ile
225                 230                 235                 240

Ile Ala Gly Gly Asn Ala Asp Ile Met Ala Thr Ala Val Lys Ile Val
                245                 250                 255

Lys Pro Gly Gly Thr Ile Ala Asn Val Asn Tyr Phe Gly Glu Gly Glu
            260                 265                 270

Val Leu Pro Val Pro Arg Leu Glu Trp Gly Cys Gly Met Ala His Lys
        275                 280                 285

Thr Ile Lys Gly Gly Leu Cys Pro Gly Gly Arg Leu Arg Met Glu Arg
    290                 295                 300

Leu Ile Asp Leu Val Phe Tyr Lys Pro Val Asp Pro Ser Lys Leu Val
305                 310                 315                 320

Thr His Val Phe Gln Gly Phe Asp Asn Ile Glu Lys Ala Phe Met Leu
                325                 330                 335

Met Lys Asp Lys Pro Lys Asp Leu Ile Lys Pro Val Val Ile Leu Ala
            340                 345                 350
```